United States Patent [19]

Amin et al.

[11] Patent Number: 5,759,836
[45] Date of Patent: Jun. 2, 1998

[54] OSTEOARTHRITIS-ASSOCIATED INDUCABLE ISOFORM OF NITRIC OXIDE SYNTHETASE

[75] Inventors: Ashok R. Amin, Union, N.J.; Steven B. Abramson, Rye, N.Y.

[73] Assignee: Hospital For Joint Diseases, New York, N.Y.

[21] Appl. No.: 410,739

[22] Filed: Mar. 27, 1995

[51] Int. Cl.$^6$ .............................. C12N 9/02; C12N 9/99
[52] U.S. Cl. ........................................ 435/189; 435/184
[58] Field of Search .................... 435/25, 172.3, 435/184, 189, 320.1; 536/23.2

[56] References Cited

U.S. PATENT DOCUMENTS 5,132,407  7/1992  Stuehr et al. .................... 530/395

OTHER PUBLICATIONS

Amin et al., "A Novel Mechanism of Action for Nonsteroidal Anti–Inflammatory Drugs: Effects on Inducible Nitric Oxide Synthetase," Arthritis & Rheumatism, Sep. 1995, vol. 38, No. 9 (Supplement), p. S344, Abstract no. 1144.

Amin et al., "The Expression and Regulation of Nitric Oxide Synthase in Human Osteoarthritis–Affected Chondrocytes: Evidence for Up–Regulated Neuronal Nitric Oxide Synthase" J. Exp. Med., Dec. 1, 1995, vol. 182, No. 6, pp. 2097–2102.

Geller et al., "Molecular Cloning and Expression of Inducible Nitric Oxide Synthase from Human Hepatocytes," Proc. Nat. Acad. Sci., USA, Apr. 1993, vol. 90, pp. 3491–3495.

Sakurai et al., "Expression of Inducible Nitric Oxide Synthase Gene in Inflammatory Arthritides," Arthritis & Rheumatism, Sep. 1994, vol. 37, No. 9 (Supplement), p. S306, Abstract No. 869.

Carl Nathan et al, Regulation of Biosynthesis of Nitric Oxide, Journal of Biological Chemistry, vol. 269, No. 19, pp. 13725–13778, May 13, 1994.

Chartrain et al Molecular Cloniing, Structure, and Chromosomal Localization of the Human Iducible Nitric Oxide Synthase Gene, Journal of Biological Chemistry, vol. 269, No. 9, pp. 6765–6772, Mar. 4, 1994.

Campbell et al, Human Articular Cartlidge ans chondrocytes Produce Hemopietic Colony–Stimualting Factors in Culture in Response to IL–1 Journal of Immunology, vol. 147, No. 4, pp. 1238–1246, Aug. 15, 1991.

Charles et al Cloning, Characterization, and Expression of a cDNA Encoding an Inducible Nitric Oxide Synthase from the Human Chondrocyte, Pro. Natl. Acad Sci USA, vol. 90, pp. 11419–11423, Dec. 1993.

Palmer et al, Induction of Nitric Oxide Synthase in Human Chondrocytes, Biochemical and Biophysical research Communications, vol. 193, No. 1, pp. 398–405, May 28, 1993.

Ghosh et al, Inhibition of NF–kB by Sodium Salicylate and Aspirin, Science, vol. 26, pp. 956–958, Aug. 12, 1994.

Tetsuka et al Cross–Talk Between Cycolooxygenase and Nitric Oxide Pathways: Prostaglandin $E_2$ Negatively Modulates Induction of Nitric Oxide Synthase by Interleukin 1, Proc. Natl. Acad. Sci. USA, vol. 91, pp. 12168–12172, Dec. 1994.

Salvemini et al, Nitric Oxide Acticvates Cyclooxygenase Enzymes, Proc. Natl. Acad. Sci. USA, vol. 90, pp. 7240–7244, Aug. 1993.

Vane et al Iducible Isoforms of Cyclooxygenase and Nitric–Oxide Synthase in Inflammation, Proc. Natl. Acad. Sci. USA, vol. 91, pp. 2046–2050, Mar. 1994.

Taskiran et al, Nitric Oxide Mediates Suppression of Cartildge Proteoglycan Synthesis by, Interleukin–1, Biochemical and Biophysical Research Communications, vol. 200, No. 1, pp. 142–148, vol. 200, No. 1, Apr. 15, 1994.

Stefanovic–Racic et al, N–Monomethyl Arginine, an Inhibitor of Nitric Oxide Synthase, Suppresses the Development of Adjuvant Arthritis in Rats, Arthritis & Rhfeumatism vol. 37, No. 7, pp. 1062–1069, Jul. 1994.

Saxne et al, Detection of Tumor Necrosis Factor but Not Tumor Necrosis factor in Rheumatoid, Arthritis Synovial Fluid and Serum, Arthitits and Rheumatism, vol. 31, No. 8, pp. 1041–1045, Aug. 1988.

Lotz et al, Transforming Growth Factor—and Cellular Immune Responses in Synovial Fluids, Journal of Immunology, vol. 144, No. 11, pp. 4189–4194, Jun. 1, 1990.

Stadler et al, Articular Chondrocytes Synthesize Nitric Oxide in Response to Cytokines and Lipopolysaccharide, Journal of Immunology, vol. 147 No. 11, pp. 3915–3920, Dec. 1, 1991.

Primary Examiner—Jon P. Weber
Attorney, Agent, or Firm—Browdy and Neimark

[57] ABSTRACT

An novel isoform of inducible nitric oxide synthase (OA-NOS) has been identified in osteoarthritis-affected articular cartilage. Some properties, including molecular weight, are similar to the constitutive isoform of neuronal nitric oxide synthase (ncnos) while other properties share similarity with the previously identified inducible nitric oxide (iNOS). Acetylating agents, such as aspirin and N-acetylimidazole act on both iNOS and OA-NOS by inhibiting their catalytic activities. A method is provided to screen for acetylating agents that inhibit OA-NOS, and the selective inhibition of OA-NOS by inhibitory agents is determined by comparison to a panel of different isoforms of nitric oxide synthase.

2 Claims, 4 Drawing Sheets

FIG. 1

LPS INDUCED

| | CONTROL | NONE | Asp 1mM | Asp 0.1mM | NaCl 1mM | Indo 5μM | EtOH 0.2%(v/v) |
|---|---|---|---|---|---|---|---|
| SPECIFIC ACTIVITY | 15 | 396 | 137 | 359 | 369 | 400 | 418 |
| % INHIBITION | — | — | 68 | 10 | 7 | 0 | 0 |

OSTEOARTHRITIS-ASSOCIATED INDUCABLE ISOFORM OF NITRIC OXIDE SYNTHETASE

BACKGROUND OF THE INVENTION

1. Field of the Invention

The present invention relates to a novel inducible nitric oxide synthase, to a method of screening compounds that inhibit the catalytic activity of the novel nitric oxide synthase, as well as to the DNA encoding the novel inducible protein, the expression vector, and host cells containing such DNA and antibodies to such a protein.

2. Description of the Background Art

Nitric oxide (NO), a recently acknowledged multifunctional mediator produced by and acting on various cells, participates in inflammatory and autoimmune-mediated tissue destruction. NO is produced by the ubiquitous enzyme nitric oxide synthase (NOS). Inflammatory processes in vivo inter-regulate the expression and function of both inducible nitric oxide synthase (iNOS) and cyclooxygenase-2 (COX-2) (Vane et al., *Proc. Natl. Acad. Sci. USA* 91:2046–2050, 1994; Salvemini, *Proc. Natl. Acad. Sci. USA* 90:7240–7244, 1993; Tetsuka et al., *Proc. Natl. Acad. Sci. USA* 91, 12168–12172, 1994). Therefore, modulation of NO synthesis and action represents a new approach to the treatment of inflammatory and autoimmune conditions (Schmidt and Walter, *Cell* 78:919–925, 1994). Human chondrocytes exposed to NO showed inhibition of growth, chemotaxis, and induced apoptosis and cell death (Blanco et al., *Arthritis Rheum.* 37 (Suppl.): S294, 1994; Clancy et al., *Arthritis Rheum.* 37 (Suppl. 9): S293, 1994]. Stimulation of chondrocytes with IL-1 in vitro is known to induce oxygen radicals, upregulation of iNOS activity and inhibition of matrix synthesis, such as proteoglycan synthesis, which can be reversed by inhibitors of iNOS (Taskiran et al., *Biochem. Biophys. Res. Comm.* 200:142–148, 1994).

NOS catalyzes the formation of NO from the terminal guanidine nitrogen atom of L-arginine (Marletta, *Cell* 78:927–930, 1994). Three major forms of NOS have been identified to date (Xie et al., *J. Biol. Chem.* 269:4705–4708, 1994). There are two forms of constitutive NOS (cNOS), one present in endothelial cells and the other in neuronal cells. The inducible NOS (iNOS), expressed in various cell types, is upregulated by lipopolysaccharide (LPS), IL-1β, IFN-γ, TNF-α, and other immunological or inflammatory stimuli. Production of NO from constitutive NOS is a key regulator of homeostasis, whereas the generation of NO by inducible NOS plays an important role in inflammation and host-defense responses.

NO formation is increased during inflammation (arthritis, ulcerative colitis, Crohn's disease), and several classic inflammatory symptoms (erythema, vascular leakiness) are reversed by NOS inhibitors (Schmidt and Walter, 1994, supra). Furthermore, unregulated NO synthesis becomes self-destructive, as is known in disorders such as autoimmune disease, immune rejection of allografted organs, graft-versus-host disease, and sepsis. However, these pro-inflammatory effects of NO are not evident under acute physiological conditions, in which it can mediate anti-inflammatory functions such as inhibition of neutrophil adhesion, COX activity, cytokine formation and osteoclastic bone resorption (Schmidt and Walter, 1994, supra).

Recent studies have indicated that NO directly modulates the activity of COX-2 through a mechanism independent of cGMP (Salvemini et al., 1993, supra). The effect of NO on COX-2 is dose-dependent. Low levels of NO activate COX. In contrast, large amounts of NO by iNOS can inhibit the induction of COX-2 and suppress the formation of COX metabolites. Salvemini and co-workers have recently demonstrated inhibition of inflammatory response by modulation of NO production in various animal models of inflammation. These in vivo studies again demonstrate the direct role of NO in inflammation and tissue destruction.

The expression and function of iNOS and COX2, known to be involved in inflammatory processes in vivo (Stadler et al., *J. Leukocyte Biol.* 53:165–172, 1993; Vane et al., 1994, supra), are regulated by the local production of cytokines (Curran et al., *J. Exp. Med.* 170:1769–1774, 1989; Nussler and Billiar, *J. Leukocyte. Biol.* 54:171–178, 1993; Schini et al., *Eur. J. Pharmacol.* 216, 379–383, 1992). This is further substantiated by the observation that the upregulation of iNOS can be reduced by anti-inflammatory cytokines such as IL-4, IL-8, IL-10, TGF-β-1, -2, and -3, and macrophage deactivating factor (Nussler and Billiar, 1993, supra). COX-2 is induced in a number of cell types by EGF (Bailey et al., *J. Lipid Res.* 26:54–61, 1985), FGF (Goddard et al., *Cytokine* 4:377–384, 1992), PDGF (Lin et al., *J. Biol. Chem.* 264:17379–17383, 1989), IL-1 (Raz et al., *Proc. Natl. Acad. Sci. USA* 86:1657–1661, 1989) and TGF-β (Bailey and Verma, *Anal. Biochem.* 196:11–18, 1991). $PGE_2$ inhibits the production of cytokines (Ferreri et al., *J. Biol. Chem.* 267:9443–9449, 1992) and cytokine-induced proliferation in a number of cell types in vitro, (Albina and Henry, *J. Surg. Res.* 50:403–409, 1991). However, the actions of PGs in vivo are more complex, in that COX inhibitors exacerbate cartilage erosion but reduce bone loss (Willoughby et al., *J. Lipid Mediators* 6:298–293, 1993). Expression of COX-1 and COX-2 is influenced by IL-1 in rheumatoid synovial tissue (Crofford et al., *J. Clin. Inv.* 93:1095–1101, 1992). IL-1 is also known to modulate the activity of COX-2 in chondrocytes, and to affect chondrocyte function by inhibiting proteoglycan and collagen (Type II) synthesis and promoting matrix degradation by stimulating neutral and metalloproteases (Lyons-Giordano et al., *Exp. Cell Res.* 206:58–62, 1993). Differing levels of NO (induced by cytokines or endotoxin) have stimulatory as well as inhibitory effects on $PGE_2$ and the synthesis of neutral proteases in chondrocytes (Stadler et al., *J. Immunol.* 147:3915–3920, 1991). IL-1 has been reported to be a strong inducer of IL-6 synthesis and secretion in human chondrocytes, and has been shown to have a protective effect on extracellular matrix of human articular chondrocytes (Günther et al., *Arthritis Rheum.* 37:395–405, 1994). Recently, Venn et al. (*Arthritis Rheum* 36:819–826, 1993) have reported elevated levels of IL-6 and TNF-α in synovial fluid of canine osteoarthritis.

In spite of the antagonistic activities of TNF-α and TGF-β, both cytokines have been implicated as contributing to local inflammatory responses in arthritis. These cytokines are present in synovial fluids of human arthritic joints (Saxne et al., *Arthritis Rheum.* 31:1041–1045, 1988; Lotz et al., *J. Immunol.* 144:4189–4194, 1990) and rodents with experimentally induced arthritis (Lafyatis et al., *J. Immunol.* 143:1142–1148, 1989; Allen et al., *J. Exp. Med.* 171:231–247, 1990). Thorbecke and co-workers have shown systemically administered TNF-α and anti-TGF-β in vivo were found to increase arthritis morbidity in the rodent system, while administration of TGF-β1 and anti-TNF afforded a significant degree of protection (Kuruvilla et al., *Proc. Natl. Acad. Sci. USA* 88:2918–2921, 1991). TGF-β exerts opposite effects from IL-1β on rabbit chondrocytes (Redini et al., *Arthritis Rheum.* 36:44–50, 1993). Furthermore, TGF-β also controls synthesis of extracellular matrix components such as collagen, fibronectin and proteoglycan (Roberts et al., *Kidney Intl.* 41:557–559, 1992).

IL-1β, TNF-α and LPS induce NO production in human, bovine and rabbit articular chondrocytes, and human osteoblasts (Ralston et al., *Endocrinology* 135:330–336, 1994), whereas IFN-γ and fibroblast growth factor (FGF) fail to provoke the production of NO but increase the potency of IL-1β (Palmer et al., *Biophys. Res. Commun.* 193:398–405, 1993). A combination of IL-1, LPS and TNF-α has been shown to induce maximum production of NO in chondrocytes (Palmer et al., 1993, supra). Glucocorticoids can block the upregulation of iNOS from human osteoblasts (Ralston et al., 1994, supra), rabbit chondrocytes and rodent macrophages (Palmer et al., *Biochem. Biophys. Res. Commun.* 188:209–215, 1992), but not of iNOS from human chondrocytes (Palmer et al., 1993, supra).

The role of NO in various animal models of rheumatoid arthritis (RA) has been demonstrated (Stefanovic-Racic et al., *Arthritis Rheum.* 37:1062–1069, 1994). Adjuvant arthritis was induced in rats; the onset of clinical symptoms was preceded by elevated biosynthesis of NO and its end products: nitrate and nitrite. Administration of $N^G$-monomethyl-L-arginine acetate (L-NMMA), which inhibits both iNOS and cNOS, blocked (in a dose-dependent manner) NO biosynthesis, paw swelling and histopathological changes in ankle joints observed during the course of the disease in vivo. This protective effect was reversed by administration of NOS substrate L-arginine, which competitively reversed the effect of L-NMMA. NO in aqueous solution decays to yield equal amounts of nitrite and nitrate, which are used as indicators of NO production. Partial inhibition of NOS by L-NMMA was sufficient to reduce paw swelling, indicating reduction in inflammation. This suggests that adjuvant arthritis in rats may be sensitive to even small reductions in NO synthesis (Stefanovic-Racic et al., 1994, supra). These experiments clearly implicate NO in the inflammatory and erosive components of adjuvant arthritis in rats.

Possible modes of action of L-NMMA include inhibiting T cell responses to bacterial epitopes in the adjuvant, restricting blood flow to the joint by constricting synovial capillaries, and preventing the intra-articular production of NO, and also decreasing the levels of PGEs. In the MRL-lpr/lpr mutant mouse, NOS inhibitors prevent anti-DNA immune complex and glomerulonephritis, and reduce the intensity of inflammatory arthritis (Weinberg et al., *J. Exp. Med.* 179:651–660, 1994).

Classically, osteoarthritis (OA), unlike rheumatoid arthritis (RA), is defined as an inherently noninflammatory disorder of movable joints characterized by deterioration of articular cartilage and the formation of new bone at the joint surfaces and margins (Hough, in *Arthritis and Allied Conditions*, D. J. McCarty and W. J. Koopman, eds., Lea & Febiger, Philadelphia and London, 1699–1723, 1993). In contrast to RA, the synovial fluid in OA typically contains few neutrophils (<3,000/mm$^3$) and, except for advanced disease, the synovium does not exhibit significant cellular proliferation nor infiltration by inflammatory leukocytes. The molecular pathogenesis of OA is increasingly understood by the elucidation of events within the articular cartilage. For example, altered dynamic equilibrium between matrix synthesis and degradation by human chondrocytes has recently been implicated as having a primary role in the degeneration of articular cartilage resulting in OA (Dingle, et al., *Anal. Rheum. Dis.* 52:292, 1993; Pelletier, et al., *Sem. Arthritis Rheum.* 20 (6 Suppl. 2):12–25, 1991). This includes upregulation of catabolic activities, such as secretion of degradative proteases, and/or downregulation of anabolic activities such as collagen and proteoglycan synthesis (Dingle, et al., 1993, supra; Pelletier, et al., 1991, supra). Cytokines such as IL-1 and TNF, which induce nitric oxide (NO) production in human chondrocytes (Palmer, et al. *Biochem. Biophys. Res. Commun.* 193:398–405, 1993), have also been implicated in the destruction of cartilage in OA (Pelletier, et al., 1991, supra).

The observations made in the rodent model can be extrapolated to human studies. Mean serum nitrite concentrations in human RA (0.44 μM/l) and human OA patients (0.213 μM/l) were significantly higher than in normal controls (0.14 μM/l). In both disease groups, synovial fluid nitrite (0.91 μM/l in RA, 0.34 μM/l in OA) was significantly higher than serum nitrite, implying NO synthesis in the joint(s). These findings implicate a role for NO in the pathogenesis of OA and RA (Farrell et al., *Ann. Rheum. Dis.* 51:1219–1222, 1992).

The most intriguing finding was that serum nitrite concentrations were increased in patients with both OA and RA, compared with controls. The origin of this nitrite is not clear; widespread synovial inflammation might increase serum nitrite when synovial fluid from the lymphatic system enters the systemic circulation and by equilibration with the vascular compartment within the synovium. This may not entirely account for the higher serum nitrite concentration in RA compared with controls, however, and seems an unlikely explanation in patients with OA. A possible source of increased nitrite is the systemic vasculature and other cells in which the induction of NO has been shown. Although difficult to reconcile with current concepts of OA, this is compatible with the systemic nature of RA, where cytokines are produced by synovial tissues (pannus) and where there is evidence for systemic circulation of cytokines (e.g., acute phase mediators and constitutional symptoms).

A host of different cytokines and other cellular mediators have been reported to be localized in the synovial fluid or tissues in RA joints. These include cytokines such as IL-1, IL-2, IL-3, IL-4, IL-5, IL-6, TNF-α, IFN-α and IFN-γ, colony stimulating factors (GM-, M-, and G-CSF), platelet-derived growth factor (PDGF), TGF-α and TGF-β (Maini, Br. J. Rheumatol. 28:466–479, 1989; Feldmann et al., *Ann. Rheum. Dis.* 49:480–486, 1990; Malemud, *Rheumatic Disease Clinics of North America* 19:569–580, 1993). Chondrocytes can produce cytokines in an autocrine and paracrine manner (Lotz et al., *J. Immunol.* 148:466–473, 1992; Seid et al., *Arth. Rheum.* 36:35–43, 1993; Guerne et al., *J. Cell. Physiol.* 158:476–484, 1994). These include IL-1, IL-6, IL-8, CSF and TGF-β (Campbell et al., *J. Immunol.* 147:1236–1246, 1991; Redini et al., 1993, supra). IL-1, TNF-α, and fibroblast growth factor (FGF) have consistently been shown to increase production of degradative proteases (gelatinase and stromelysin) with a mixed effect on anabolic functions in chondrocytes (reviewed: Verbruggen and Veys, In *Biological Regulation of the Chondrocytes*, M. Adolphe (Ed.), CRC Press, pp. 275–294, 1992), which includes inhibition of tissue repair by collagenase leading to destruction of the cartilage matrix in arthritis (Harvey et al., *Biochem. J.* 292:129–136, 1993). Recent studies have demonstrated that upregulation of iNOS in rabbit chondrocytes with IL-1α, in vitro cause inhibition of matrix synthesis (Taskiran et al., 1994, supra). Addition of L-NMMA, a competitive inhibitor of NOS restored proteoglycan synthesis by the chondrocytes.

The role of cytokines in OA cartilage degradation is not well defined (Pelletier et al., *Sem. Arthritis Rheum.* 20 (6 Suppl. 2):12–25, 1991; Pelletier et al., *Rheumatic Disease Clinics of North America* 19 (3):545–568, 1993). However, there is some evidence to support that speculation that cytokines such as IL-1 (Sano et al., *J. Clin. Inv.* 89:97–108, 1992; Szczepanski et al., *Arthritis Rheum.* 37:495–503, 1994), TNF-α and IL-6 (Pelletier et al., 1993, supra; Campbell, *Biochem. Biophys. Acta* 1182:57–63, 1993; Venn et al., 1993, supra) may play a role in OA. IL-1 has been observed in the upper half of the cartilage in both chondrocytes and the extracellular matrix (Shinmei et al., *J. Rheumatol.* 18 (Suppl):32–34, 1989). These findings indicate that the presence of IL-1 in OA tissue, associated with the fact that IL-1 induces reabsorption of cartilage both in vitro (Campbell et al., *Biochem. Biophys. Acta.* 967:183–194, 1988; Campbell et al., *Arthritis Rheum.* 33:542–352, 1990) and in vivo (Henderson and Pettipher, *Clin. Exp. Immunol.* 75:306–310, 1989) makes its involvement in the pathophysiology of OA very likely.

Eight cDNA sequences have been reported deriving from three known NOS genes in 4 species (Nathan and Xie, *J. Biol. Chem.* 269:13725–13728, 1994). Human chromosome 17cen-q11.2 houses the 26-exon, 37 kb iNOS gene. Billiar et al. have demonstrated that hepatocyte and chondrocyte iNOS cDNA have >99% homology, with a difference of only 12 out of 4000 base pairs (Chartrain et al., *J. Biol. Chem.* 269:6765–6772, 1994; Charles et al., *Proc. Natl. Acad. Sci. USA* 90:11419–11423, 1993). Furthermore, in situ data also indicate that they are present on the same locus on a single chromosome, thus indicating that there is a single gene for iNOS in humans. Analysis of human iNOS promoter associated with cardiovascular homeostasis (vascular smooth muscle cells), and comparison with hepatocyte iNOS promoter, indicates that they are similar. The identity of about 1.1 kb upstream of the TATA box between human iNOS and murine iNOS gene decreases to <60%, due to the difference between the species. Likewise, the murine iNOS is also a single, homologous iNOS gene. The currently published data, however, exclude the existence of a novel iNOS gene that is divergent from the human/murine iNOS cDNA currently isolated.

While non-steroidal anti-inflammatory drugs (NSAIDs), which include aspirin and sodium salicylate, share the important property of inhibiting prostaglandin biosynthesis, these actions are by no means sufficient to explain all the anti-inflammatory effects of NSAIDs. NSAIDs also inhibit activation of neutrophils (Abramson et al., *Biochem. Pharmacol.* 47, 593–572, 1994), which provoke inflammation by releasing products other than prostaglandins (Abramson et al., *Proc. Natl. Acad. Sci. USA* 82, 7227–7231, 1985). Furthermore, NO has recently been reported to modulate the activity of prostaglandin endoperoxide H synthase-2 (cyclooxygenase-2, or COX-2) in a concentration-dependent manner, through a mechanism independent of cGMP (Salvemini et al., *Proc. Natl. Acad. Sci. USA* 90, 7240–7244, 1993), and recently Vane and co-workers have implicated NO as an important mediator of inflammation in animal models (Vane et al., *Proc. Natl. Acad. Sci. USA* 91, 2046–2050, 1994). It is known that transcription factor (NF-κB) is critical for the induction and expression of multiple cellular and viral genes involved in inflammation/infection and induction of IL-1, IL-6 and adhesion molecules. Kopp and Ghosh (*Science* 265:956–959, 1994) have recently demonstrated that sodium salicylate and aspirin (at suprapharmacological concentrations: 5–20 mM) interfere in the activation of NF-κB.

NO is a vital component of host defense, but potentially toxic under pathological conditions such as arthritis. Changes in NO concentration within a cell or the microenvironment switches it from friend to foe, and vice versa. Previous observations in the literature suggest that inflammatory cytokine-mediated pathogenesis is an integral component, yet to be acknowledged, of the pathophysiology of OA, in spite of the fact that OA joints commonly do not manifest clinical signs of inflammation. There is overwhelming evidence in the literature that NO, a recently recognized inflammatory component, is one of the key factors that participate in the pathological conditions observed in RA.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention is based on the discovery of a novel form of inducible nitric oxide synthase (OA-NOS). It is further based on the discovery that acetylating agents can inhibit the catalytic activity of inducible nitric oxide synthase (iNOS) and OA-NOS by donating an acetyl group to such a NOS enzyme or to a cofactor/precursor that is required for enzymic activity of NOS.

Accordingly, it is an object of the invention is to provide a novel inducible nitric oxide synthase (OA-NOS), obtainable from osteoarthritis-affected or rheumatoid-arthritis-affected articular cartilage.

Another object of the invention is to provide antibodies specific for the novel inducible OA-NOS.

A further object of the invention is to provide a recombinant DNA molecule encoding for the novel inducible OA-NOS.

Still another object of the invention is to provide a method of screening acetylating agents that are inhibitory to the inducible/OA isoforms of nitric oxide synthase.

Yet another object of the invention is to provide a method of testing for agents which can selectively inhibit OA-NOS without significantly affecting iNOS and constitutive NOS isoforms.

Additional aspects and embodiments of the invention are set forth or readily arise from the drawings described below or from the following detailed description of the invention.

BRIEF DESCRIPTION OF THE DRAWINGS

FIG. 1 shows the effect of NSAIDs on iNOS activity in cell-free extracts. RAW 264.7 cells were induced with LPS for 16 h and enzyme extracts were prepared to examine iNOS activity in cell-free extracts by monitoring the conversion of L-[$^3$H]-arginine to L-[$^3$H]-citrulline by thin layer chromatography (TLC) as described in Experiment 1. NSAIDs were preincubated with the enzyme extracts 20 min prior to starting the reaction, and the formation of L-[$^3$H]-citrulline was monitored for 1 h before it was terminated. Equivalent volume of alcohol that was used as a solvent for NSAIDs was also added as an additional control. The data represent the TLC analysis of one of 2 similar experiments. The percent inhibition is determined after removing the control value (=15), which represents specific activity of iNOS in uninduced cells. The specific activity of LPS-treated cells after 16–18 h was found to be 396 picomoles of [$^3$H]-citrulline released/min/mg protein.

FIGS. 5A and B show the effect of NSAIDs on iNOS expression in rat chondrosarcomas and human OA cartilage. NSAIDs were tested in: (FIG. 5A) rat chondrosarcomas stimulated with LPS, and (FIG. 5B) unstimulated OA cartilage (n=3). Aspirin, NaSal, L-NMMA (500 µM) and tenidap showed significant inhibition of iNOS in rat chondrosarcomas, whereas aspirin and NaSal blocked iNOS expression in OA cartilage. Furthermore, note the inhibition of OA-iNOS by 5 µM of indomethacin and lack of significant effect (as compared to LPS) in rat chondrosarcomas at 20 µM concentration.

DETAILED DESCRIPTION OF PREFERRED EMBODIMENTS

Figure 2:
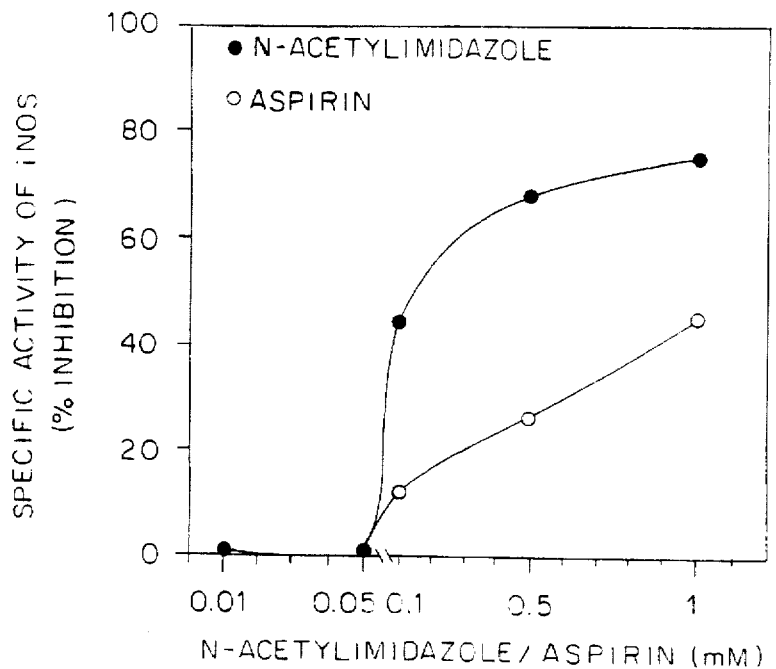
FIG. 2 shows the effect of acetylating agents aspirin and N-acetylimidazole on the catalytic activity of iNOS in cell-free extracts. The enzyme reactions were set up as described in FIG. 2. Acetylating compounds were incubated with the enzyme extracts 20 min prior to starting the reaction, and assayed as described in Experiment 1. The specific activity of LPS-treated cells after 16–18 h was found to be 178 picomoles of [$^3$H]-citrulline released/min/mg protein. Equivalent volume of ethanol, which was used as a carrier for the drugs, inhibited iNOS activity by ~10% in this experiment.

The present invention concerns a novel isoform of nitric oxide synthase (NOS) that is inducible, and is also based on the discovery that the catalytic activity of inducible isoforms of NOS are inhibited by acetylation. This discovery of a novel isoform of inducible NOS is surprising in view of the widely-held belief in the art that only one isoform of inducible NOS is present in human cells.

The novel inducible NOS of the invention is designated herein as "osteoarthritis-affected NOS" (OA-NOS) to distinguish it from the previously-known inducible NOS (iNOS). Like iNOS, OA-NOS is also inducible and shares with it some other similar biochemical properties, such as sensitivity to certain inhibitors of iNOS. However, OA-NOS also differs from iNOS in size and in being insensitive to other iNOS inhibitors, such as TGF-β and hydrocortisone, characteristics that by themselves make OA-NOS similar to a constitutive neuronal isoform of NOS (ncNOS).

More specifically, OA-NOS is characterized first of all by its ability of being obtainable from osteoarthritis-affected articular cartilage. It has a size of about 155–160 kD. It cross-reacts with antibodies raised against eNOS but not with antibodies raised against iNOS. It complexes with calmodulin. OA-NOS shows sensitivity to cycloheximide, aspirin, indomethacin, sodium salicylate, cyclosporin, PDTC, aminoguanidine, and L-NMMA, although it is not sensitive to TGF-β or hydrocortisone. It is inducible by cytokines and endotoxin.

OA-NOS may be purified from osteoarthritis-affected articular cartilage by any known technique. For example, the OA-NOS may be extracted from slices of articular cartilage, frozen and milled to a fine particulate in liquid nitrogen, with neutral salt buffer containing protease inhibitors. This extract can be loaded into an α-iNOS monoclonal antibody-Sepharose 4B column and the OA-NOS separated by affinity chromatography. The OA-NOS can then be isolated by elution with glycine-HCl (pH 2–3). Once a sufficient quantity of purified OA-NOS is obtained, it may be sequenced and standard techniques used to clone it using degenerate probes based on the amino acid sequence, by probing a cDNA or genomic DNA library.

The novel inducible OA-NOS is obtainable from osteoarthritis-affected articular cartilage and, according to the present invention, the catalytic activity of both OA-NOS and iNOS were found to be inhibited by acetylation.

It will be appreciated that OA-NOS as well as iNOS can serve as acetylation-sensitive markers for screening a variety of acetylating agents, such as aspirin and N-acetylimidazole, that can donate an acetyl group to OA-NOS, iNOS or other NOS to inhibit their catalytic activity. While other available methods to specifically screen for acetylation of proteins can be used or adapted to screen for acetylation of OA-NOS or iNOS, the preferred method for screening the effectiveness of potential acetylating agents, or other potentially inhibitory agents to be tested, is through the use of an organ culture, taken from slices of osteoarthritis-affected or rheumatoid-arthritis-affected articular cartilage containing induced OA-NOS, preferably maintained for 24–72 hours in the presence or absence of acetylating or other inhibitory/ modulating agents. Levels of nitrite, which is indicative of OA-NOS activity, and of $PGE_2$ (indicative of COX2 activity) can be directly measured for inhibition of OA-NOS and COX2 activity by acetylation. Inhibition of COX2 activity serves as a built-in control for inhibition of catalytic activity by acetylation. Other inhibitory agents that are non-acetylating can also be screened by this organ culture assay method where two inflammatory components, OA-NOS and COX2, are used as readouts in this assay.

A DNA molecule encoding the inducible OA-NOS of the present invention can be obtained by cDNA cloning, and in a preferred embodiment, the cDNA will be incorporated into a replicable expression vehicle such as a plasmid vector capable of autonomous replication in recipient host cells. Human chondrosarcoma cells (which lack NOS activity) can be used to transiently express OA-NOS.

By "cloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

By "cDNA" is meant complementary DNA produced from an RNA template by the action of RNA-dependent DNA polymerase (reverse transcriptase). Thus a "cDNA clone" means a duplex DNA sequence complementary to an RNA molecule of interest, carried in a cloning vector.

By "cDNA library" is meant a collection of recombinant DNA molecules containing cDNA inserts which together comprise the entire expressible genome of an organism. Such a cDNA library may be prepared by methods known to those of skill, and described, for example, in Ausubel et al., infra and Sambrook et al., infra. Generally, RNA is first isolated from the cells of an organism from whose genome it is desired to clone a particular gene. Preferred for the purposes of the present invention are human chondrocytes from osteoarthritis-affected or rheumatoid-arthritis-affected articular cartilage.

Standard reference works setting forth the general principles of recombinant DNA technology include Ausubel et al., eds., *Current Protocols In Molecular Biology*, Green Publishing Assoc. and Wiley Interscience, N.Y. (1987–1994), Watson et al., *Molecular Biology of the Gene*, Volumes I and II, The Benjamin/Cummings Publishing Company, Inc., publisher, Menlo Park, Calif. (1987); Darnell et al., *Molecular Cell Biology*, Scientific American Books, Inc., publisher, New York, N.Y. (1986); Lewin, *Genes II*, John Wiley & Sons, publishers, New York, N.Y. (1985); Old et al., *Principles of Gene Manipulation: An Introduction to Genetic Engineering*, 2d edition, University of California Press, publisher, Berkeley, Calif. (1981); and Sambrook et al., *Molecular Cloning: A Laboratory Manual*, Cold Spring Harbor Laboratory, Cold Spring Harbor, N.Y. (1989). These references are hereby incorporated by reference.

In order to be capable of expressing the OA-NOS protein, an expression vector should comprise also specific nucleotide sequences containing transcriptional and translational regulator information linked to the DNA coding for the desired protein in such a way as to permit gene expression and production of the protein. First, in order for the gene to be transcribed, it must be preceded by a promoter recognizable by RNA polymerase, to which the polymerase binds and thus initiates the transcription process. There are a variety of such promoters in use, which work with different efficiencies (strong and weak promoters). They are different for prokaryotic and eukaryotic cells.

The promoters that can be used in the present invention may be either constitutive, for example, the int promoter of bacteriophage lambda, the bla promoter of the β-lactamase gene of pBR322, and the CAT promoter of the chloramphenicol acetyl transferase gene of pPR325, etc., or inducible, such as the prokaryotic promoters including the major right and left promoters of bacteriophage lambda ($P_l$ and $P_r$), the trp, recA, lacZ, lacI, ompF and gal promoters of *E. coli*, or the trp-lac hybrid promoter, etc. (Glick, *J. Ind. Microbiol.* 1:277–282, 1987).

Besides the use of strong promoters to generate large quantities of MRNA, in order to achieve high levels of gene expression in prokaryotic cells, it is necessary to use also ribosome-binding sites to ensure that the mRNA is efficiently translated. One example is the Shine-Dalgarno sequence (SD sequence) appropriately positioned from the initiation codon and complementary to the 3'-terminal sequence of 16S RNA.

For eukaryotic hosts, different transcriptional and translational regulator sequences may be employed, depending on the nature of the host. They may be derived from viral sources, such as adenovirus, bovine papilloma virus, Simian virus, or the like, where the regulatory signals are associated with a particular gene which has a high level of expression. Examples are the TK promoter of Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the OA-NOS of the invention, and the operably linked transcriptional and translational regulator signals is inserted into a vector which is capable of integrating the desired gene sequences into the host cell chromosome. In order to be able to select the cells which have stably integrated the introduced DNA into their chromosomes, one or more markers which allow for selection of host cells which contain the expression vector is used. The marker may provide for prototropy to an auxotrophic host, biocide resistance, e.g., antibiotics, or heavy metals, such as copper, or the like. The selectable marker gene can either be directly linked to the DNA gene sequences to be expressed, or introduced into the same cell by cotransfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Mol. Cel. Biol.* 3:280, 1983.

In a preferred embodiment, the introduced DNA molecule will be incorporated into a plasmid or viral vector capable of autonomous replication in the recipient host. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli*, for example, pBR322, ColE$_1$, pSC101, pACYC 184, etc. (see Maniatis et al., op. cit.); Bacillus plasmids such as pC194, pC221, pT127, etc. (Gryczan, *The Molecular Biology of the Bacilli*, Academic Press, New York, pp. 307–329, 1982); Streptomyces plasmids including pIJ101 (Kendall et al., *J. Bacteriol.* 169:4177–4183, 1987); Streptomyces bacteriophages such as φC31 (Chater et al., in *Sixth International Symposium on Actinomycetales Biology*, Akademiai Kaido, Budapest, Hungary, pp. 45–54, 1986), and Pseufdomonas plasmids (John et al., *Rev. Infect. Dis.* 8:693–704, 1986, and Izaki, *Jpn. J. Bacteriol.* 33:729–742, 1978).

Preferred eukaryotic plasmids include BPV, vaccinia, SV40, 2-micron circle, etc., or their derivatives, such as pcDNA3 or pRc/CMV (Invitrogen, San Diego, Calif.). Such plasmids are well known in the art (Botstein et al., *Miami Wint. Symp.* 19:265–274, 1982; Broach, in *The Molecular Biology of the Yeast Saccharomyces: Life Cycle and Inheritance*, Cold Spring Harbor Laboratory, Cold Spring Harbor, N.Y., pp. 445–470, 1981; Broach, *Cell* 28:203–204, 1982; Bollon et al., *J. Clin. Hematol. Oncol.* 10:39–48, 1980; Maniatis, in *Cell Biology: A Comprehensive Treatise*, Vol. 3: *Gene Expression*, Academic Press, New York, pp. 563–608, 1980).

Once the vector or DNA sequence containing the construct(s) has been prepared for expression, the expression vector may be introduced into an appropriate host cell by any variety of suitable means, such as transformation, transfection, lipofection, conjugation, protoplast fusion, electroporation, calcium phosphate precipitation, direct microinjection, etc.

Host cells to be used in this invention may be either prokaryotic or eukaryotic. Preferred pyokaryotic hosts include bacteria such as *E. coli*, Bacillus, Streptomyces, Pseudomonas, Salmonella, Serratia, etc. The most preferred prokaryotic host is *E. coli*. Bacterial hosts of particular interest include *E. coli* K12 strain 294 (ATCC 31446), *E. coli* X1776 (ATCC 31537), *E. coli* W3110 (F-, lambda-, prototrophic (ATCC 27325)), and other enterobacterium such as Salmonella typhimurium or Serratia narcescens and various Pseudomonas species. Under such conditions, the protein will not be glycosylated. The prokaryotic host must be compatible with the replicon and control sequences in the expression plasmid.

However, eukaryotic hosts are preferred over prokaryotic hosts. Preferred eukaryotic hosts are mammalian cells, e.g., human, monkey, mouse and chinese hamster ovary (CHO) cells, because they provide post-translational modifications to protein molecules including correct folding, correct disulfide bond formation as well as glycosylation at correct sites. Also yeast cells and insect cells can carry out post-translational peptide modifications including high mannose glycosylation. A number of recombinant DNA strategies exist which utilize strong promoter sequences and high copy number of plasmids which can be utilized for production of the desired proteins in yeast and in insect cells. Yeast cells recognize leader sequences on cloned mammalian gene products and secrete peptides bearing leader sequences.

After the introduction of the vector, the host cells are grown in a selective medium, which selects for the growth of vector-containing cells. Expression of the cloned gene sequence(s) results in the production of the OA-NOS. The expressed protein is then isolated and purified by any conventional procedure involving extraction, precipitation, chromatography, electrophoresis, or the like, or by affinity chromatography, using ncNOC or anti-OA-NOS monoclonal antibodies immobilized on a gel matrix contained within a column. Crude preparations containing the recombinant OA-NOS are passed through the column whereby the OA-NOS will be bound to the column by the specific antibody while the impurities will pass through. After washing, the protein is eluted from the gel at a high pH, e.g., pH 11.

This invention is also directed to an antibody specific for an epitope of OA-NOS. The antibodies may be used to disrupt the action of OA-NOS, thereby preventing or treating diseases associated with the presence, overproduction, or inappropriate production or action of OA-NOS in osteoarthritis and rheumatoid arthritis. Additionally, the antibodies of the present invention can be used in methods to detect the presence of, or measure the quantity or concentration of, OA-NOS in a cell or tissue extract, or a biological fluid. The antibodies may also be used in methods for measuring induction of expression of OA-NOS in a cell or in methods for identifying a compound capable of inducing the expression of OA-NOS in a cell.

It should be understood that when the term "antibodies" is used with respect to the antibody embodiments of the present invention, this is intended to include intact antibodies, such as polyclonal antibodies or monoclonal antibodies (mAbs), as well as proteolytic fragments thereof such as the Fab or F(ab')$_2$ fragments. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar, Z. et al., *Br. J. Cancer Suppl.*, 10:27–9 (1990); Gross, G. et al., *Proc. Natl. Acad. Sci. USA*, 86:10024–8 (1989)). Single chain antibodies can also be produced and used. Single chain antibodies can be single chain composite polypeptides having antigen binding capabilities and comprising a pair of amino acid sequences homologous or analogous to the variable regions of an immunoglobulin light and heavy chain (linked V$_H$-V$_L$ or single chain F$_V$). Both V$_H$ and V$_L$ may copy natural monoclonal antibody sequences or one or both of the chains may comprise a CDR-FR construct of the type described in U.S. Pat. No. 5,091,513 (the entire contents of which are hereby incorporated herein by reference). The separate polypeptides analogous to the variable regions of the light and heavy chains are held together by a polypeptide linker. Methods of production of such single chain antibodies, particularly where the DNA encoding the polypeptide structures of the V$_H$ and V$_L$ chains are known, may be accomplished in accordance with the methods described, for example, in U.S. Pat. Nos. 4,946,778, 5,091, 513 and 5,096,815, the entire contents of each of which are hereby incorporated herein by reference.

A "molecule which includes the antigen-binding portion of an antibody," is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

In order to predict antigenic epitopes present in OA-NOS, the amino acid sequence can be obtained from the cDNA of the OA-NOS or from the purified protein itself and can be inspected visually or analyzed by computer, for example, using the program of PEPTIDESTRUCTURE (Jameson et al., CABIOS 4: 181–186 (1988)). This program allows determination of hydropathicity values which are then used to determine which peptide sequences within the overall protein sequence are likely to be most immunogenic based on their potential secondary structure. Such peptides may be synthesized chemically, or alternatively, and preferably, by recombinant DNA methods.

One of the pitfalls of generating antibodies to synthetic peptides is the possibility that an antibody so raised may fail to react with the native protein. For this reason, alternative approaches may be used. The OA-NOS protein may be expressed and produced in human chondrosarcoma cells by using an appropriate expression plasmid, or protein may be isolated directly from osteoarthritis-affected cartilage (see Example 3, below). The purified protein is employed for the immunization of rabbits. Alternatively, such a protein, or a synthetic peptide, may be used to immunize a rodent for generation of a monoclonal antibody.

Polyclonal antibodies are heterogeneous populations of antibody molecules derived from the sera of animals immunized with an antigen.

Monoclonal antibodies (mAbs) are a substantially homogeneous population of antibodies to specific antigens. MAbs may be obtained by methods known to those skilled in the art. See, for example Kohler and Milstein, Nature 256:495–497 (1975); U.S. Pat. No. No. 4,376,110; Ausbel et al., eds., supra; Harlow and Lane, ANTIBODIES: A LABORATORY MANUAL, Cold Spring Harbor Laboratory (1988); and Colligan et al., eds., Current Protocols in Immunology, Green Publishing Assoc., and Wiley Interscience, New York, (1993), the contents of which reference are incorporated entirely herein by reference. Such antibodies may be of any immunoglobulin class including IgG, IgM, IgE, IgA, GILD and any subclass thereof. The hybridoma producing the mabs of this invention may be cultivated in vitro (see Example 3) or in vivo. High titers of mAbs can be obtained in in vivo production where cells from the individual hybridomas are injected intraperitoneally into pristane-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules, the different portions of which are derived from different animal species, such as those having a variable region derived from a murine mAb and a human immunoglobulin constant region. Chimeric antibodies are primarily used to reduce immunogenicity in application and to increase yields in production, for example, where murine mAbs have higher yields from hybridomas but higher immunogenicity in humans, such that human/murine chimeric mabs are used. Chimeric antibodies and methods for their production are known in the art (Cabilly et al., Proc. Natl. Acad. Sci. USA 81:3273–3277, 1984; Morrison et al., Proc. Natl. Acad. Sci. USA 81:6851–6855, 1984; Boulianne et al., Nature 312:643–646, 1984; Cabilly et al., European Patent Application 125.023 (published Nov. 14, 1984); Neuberger et al., Nature 314:268–270, 1985; Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Morrison et al., European Patent Application 173494 (published March 5, 1986); Sahagan et al., J. Immunol. 137:1066–1074, 1986; Robinson et al., International Patent Publication WO 9702671 (published May 7, 1987); Liu et al., Proc. Natl. Acad. Sci USA 84:3439–3443, 1987; Sun et al., Proc. Natl. Acad. Sci. USA 84:214–218, 1987; Better et al., Science 240:1041–1043, 1988; and Harlow and Lane, ANTIBODIES: A LABORATORY MANUAL, supra. These references are hereby incorporated by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may bear structural similarity to the original mAb which induced the anti-Id. Thus, by using antibodies to the idiotypic determinants of a mAb, it is possible to identify other clones expressing antibodies of identical specificity.

Accordingly, mAbs generated against the OA-NOS protein of the present invention may be used to induce anti-Id antibodies in suitable animals, such as Balb/c mice. Spleen cells from such immunized mice are used to produce anti-Id hybridomas secreting anti-Id mabs. Further, the anti-Id mAbs can be coupled to a carrier such as keyhole limpet hemocyanin (KLH) and used to immunize additional Balb/c mice. Sera from these mice will contain anti-anti-Id antibodies that have the binding properties of the original mAb specific for an OA-NOS protein epitope.

As mentioned above, the term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of OA-NOS protein according to the methods disclosed herein for intact antibody molecules. Such fragments are typically produced by proteolytic cleavage, using enzymes such as papain (to produce Fab fragments) or pepsin (to produce F(ab')$_2$ fragments).

The antibodies, or fragments of antibodies, of the present invention may be used to quantitatively or qualitatively detect the presence of cells which express the OA-NOS protein. This can be accomplished by immunofluorescence techniques employing a fluorescently labeled antibody (see below) coupled with light microscopic, flow cytometric, or fluorimetric detection.

The antibodies of the present invention may be employed histologically, as in immunofluorescence or immunoelectron microscopy, for in situ detection of OA-NOS protein. In situ detection may be accomplished by removing a histological (cell or tissue) specimen from a subject and providing the labeled antibody of the present invention to such a specimen. The antibody (or fragment) is preferably provided by applying or by overlaying on the biological sample. Through the use of such a procedure, it is possible to determine not only the presence of the OA-NOS protein but also its distribution on the examined tissue. Using the present invention, those of ordinary skill will readily perceive that any of a wide variety of histological methods (such as staining procedures) can be modified in order to achieve such in situ detection.

Additionally, the antibody of the present invention can be used to detect the presence of soluble OA-NOS molecules in a biological sample. Used in this manner, the antibody can serve as a means to monitor the presence and quantity of OA-NOS proteins in a subject having osteoarthritis or rheumatoid arthritis.

Such immunoassays for OA-NOS protein typically comprise incubating a biological sample, such as a biological fluid, a tissue extract, freshly harvested cells, or cells which have been incubated in tissue culture, in the presence of a detectably labeled antibody capable of identifying OA-NOS protein, and detecting the antibody by any of a number of techniques well-known in the art.

The biological sample may be treated with a solid phase support or carrier (which terms are used interchangeably herein) such as nitrocellulose, or other solid support which is capable of immobilizing cells, cell particles or soluble proteins. The support may then be washed with suitable buffers followed by treatment with the detectably labeled OA-NOS-specific antibody. The solid phase support may then be washed with the buffer a second time to remove unbound antibody. The amount of bound label on said solid support may then be detected by conventional means.

By "solid phase support or carrier" is intended any support capable of binding antigen or antibodies. Well-known supports, or carriers, include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

The binding activity of a given lot of anti-OA-NOS antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the OA-NOS-specific anti-body can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect OA-NOS protein through the use of a radioimmunoassay (RIA) (Chard, T., "An Introduction to Radioimmune Assay and Related Techniques" (In: Work, T. S., et al., *Laboratory Techniques in Biochemistry in Molecular Biology*, North Holland Publishing Company, New York (1978), incorporated by reference herein). The radioactive isotope can be detected by such means as the use of a gamma counter or a liquid scintillation counter or by autoradiography. Radioactively labeled antibodies or antibody fragments can also be used for their capacity to kill cells bound by such antibodies, or cells in the immediate vicinity which are exposed to the radiation from such antibodies.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay. In a typical immunometric assay, a quantity of unlabeled antibody (or fragment of antibody) is bound to a solid support and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to "extract" the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

Antibodies or other molecules which include the antigen-binding portion of an antibody may also be used for isolation and purification of OA-NOS. Thus, for example, antibodies specific to OA-NOS can be immobilized on a solid phase support or carrier with which an impure solution containing OA-NOS is brought into contact. The OA-NOS will bind to the antibodies which are in turn bound to the support while all of the contaminants are washed away. Pure OA-NOS can then be eluted from the support by means well-known in the art.

While aspirin has been known to inhibit iNOS, prior to the present invention the specific mode of action of aspirin for this inhibition was not known. It has now been discovered that it is the acetylation capability of aspirin which causes the inhibition of iNOS and the same is true with respect to the inhibition of OA-NOS.

In order to assay for an acetylating agent having a more pronounced inhibiting effect than aspirin, and perhaps a more specific acetylating effect, one may assay such acetylating agents for their inhibiting effect on iNOS and/or OA-NOS. While any experimental model to determine the inhibiting effect on iNOS and/or OA-NOS activity may be used for the purpose of a such a drug-screening assay, a preferred embodiment for an experimental model is as follows.

An organ culture, taken from slices of osteoarthritis-affected or rheumatoid-arthritis-affected articular cartilage containing induced OA-NOS, is preferably maintained for 24–72 hours in the presence or absence of acetylating or other inhibitory/modulating agents. Levels of nitrite, which is indicative of OA-NOS activity, and of $PGE_2$ (indicative of COX2 activity) can be directly measured for inhibition of OA-NOS and COX2 activity by acetylation. Inhibition of COX2 activity serves as a built-in control for inhibition of catalytic activity by acetylation. Other inhibitory agents that are non-acetylating can also be screened by this organ culture assay method where two inflammatory components, OA-NOS and COX2, are used as readouts in this assay. Similar models for testing the activity of iNOS are well-known and may also be used for this purpose.

As various NOS are ubiquitous in the body, it would be very useful to find a therapeutic agent which is specific to OA-NOS to the exclusion of inhibiting iNOS or ncNOS. Therapeutic agents which potentially have this specificity may be assayed by screening them for inhibition against a bank of different NOSs including OA-NOS and one or more of iNOS and ncNOS. Any agent or modality which is specific for OA-NOS may then be selected. Models for measuring inhibition of iNOS and ncNOS are known in the prior art and may be used as part of this bank of tests. Any experimental model which measures the activity of OA-NOS may be used in this bank, preferably the one described above.

It should be understood that the catalytic activity of OA-NOS can also be inhibited by agents that do not acetylate OA-NOS. For instance, the binding of OA-NOS specific antibody molecules to OA-NOS may disrupt and inhibit the catalytic activity of OA-NOS. Along with acetylating agents that are shown to inhibit OA, any other agents that can inhibit the catalytic activity of OA, such as the antibody molecules of the present invention, can be tested against OA-NOS, iNOS and the constitutive NOS isoforms (ncNOS, ecNOS) to determine whether any of these agents tested are selectively inhibitory to OA-NOS alone.

The invention will now be illustrated by the following non-limiting examples.

EXAMPLE 1

The Mode of Action of Aspirin-Like Drugs and Their Effect on Inducible/OA Nitric Oxide Synthase in RA and OA Among the agents studied in an effort to elucidate the effect of NSAIDs on iNOS expression and function, we have selected three: an acetylated salicylate (aspirin, an effective inhibitor of COX); a non-acetylated salicylate (sodium salicylate, an ineffective inhibitor of COX); and a non-acetylated nonsteroidal compound (indomethacin, a potent inhibitor of COX). Aspirin, sodium salicylate and indomethacin, which reach therapeutic concentrations in plasma of 1–3 mM, 1–3 mM, and 5–20 µM, respectively (Gilman et al., Goodman and Gilman's *The Pharmacological Basis of Therapeutics*, 1993), were tested for their capacity to inhibit iNOS expression/catalytic activity at the clinically relevant concentrations.

In this example, the following material and methods were used:

Cell Lines and Reagents. Murine macrophage cells (RAW 264.7) were obtained from ATCC (Rockville, Md.). An anti-murine iNOS antibody was obtained from Transduction Laboratories (Lexington, Ky.). It was specific for murine macrophage iNOS and did not cross-react with the endothelial or brain NOS.

Western Blot Analysis. Equal amounts of protein (50 µg) estimated by BCA reagent (Pierce, Rockford, Ill.) were loaded onto SDS-PAGE gels and stained to verify the concentrations of various protein fractions by examining the intensities of the protein bands on the gels. Western blot analysis was carried out from the same cell extracts. The Western-blotted membrane was probed with a specific anti-iNOS monoclonal antibody, as specified by Transduction Laboratories (Lexington, Ky.). The blots were developed using the ECL Western blot system (Amersham, Arlington Heights, Ill.). Quantitation of the bands was performed using a densitometer from Molecular Dynamics (Sunnyville, Calif.).

Northern Blot Analysis. Total RNA was isolated using TRI Reagent (MRC Inc., Cincinnati, Ohio). Northern blot analysis was carried out as described by Church and Gilbert (*Proc. Natl. Acad. Sci. USA* 81, 1991–1995, 1994). 30 µg of RNA was subjected to electrophoresis in 1% agarose formaldehyde gel. The gel was then transferred via capillary action onto a nylon membrane (Zeta Probe, Bio-Rad Laboratories, Melville, N.Y.). The membrane was hybridized with [$^{32}$P]-dCTP-labelled iNOS cDNA (4 kb Sma I fragment), a kind gift from Dr. James Cunningham (Harvard Medical School, Boston, Mass.). After hybridization, the blot was exposed to Kodak X-ray film (Kodak, Rochester, N.Y.) for 24–48 h with intensifying screens at −70° C. The β-actin probe was purchased from ClonTech (Palo Alto, Calif.) and probed as described above. Quantitation of the intensity of the iNOS/β-actin bands was performed using a phosphoimager (Molecular Dynamics, Sunnyville, Calif.).

Assays for iNOS in Cell-Free Extracts. Specific activity of iNOS was determined in cell-free extracts by monitoring the conversion of L-[$^3$H]-arginine to L-[$^3$H]-citrulline as described by Misko et al. (*Eur. J. Pharmacol.* 233, 199–125, 1993). The reaction mixture for iNOS assay (in cell-free extracts) consists of Tris 50 µM (pH 7.8); BSA 1 mg/ml; DTT 1 mM; CaCl$_2$, 2 mM; FAD 10 µM; BH$_4$ 10 µM; L-arginine 30 µM; NADPH 1 mM. The assay mixture for cNOS consists of Tris 50 mM (pH 7.8); L-arginine 50 µM; calmodulin 10 µg/ml; BH$_4$ 10 µM; CaCl$_2$ 2 mM; NADPH 100 µM. RAW 264.7 cells were induced with LPS in the presence and absence of NSAIDs for 16–18 h. Following induction, the cells were harvested and resuspended in ice-cold saline containing 25 mM glucose. Cells were re-pelleted at 4° C. and resuspended in Tris buffer (10 mM, pH 7.4) containing 1 mg/ml each chymostatin, antipain, leupeptin and pepstatin, 1 mM DTT and 1 mM PMSF. Cells were lysed in a Polytron PT 1200 homogenizer (Kinematica AG, Switzerland) after 3 cycles of rapid freeze-thawing. The lysate was centrifuged at 16,000 rpm for 60 min at 4° C., and the supernatants were used as cell-free extracts. The reaction mixture for iNOS assay consists of Tris 50 µM (pH 7.8); BSA 1 mg/ml; DTT 1 mM; CaCl$_2$, 2 mM; FAD 10 µM; BH$_4$ 10 µM; L-arginine 30 µM; NADPH 1 mM (Abramson et al., 1985, supra). The reaction mixture was spiked with 1 µl (250 nM) of L-[$^3$H]-arginine (Dupont NEN, Boston, Mass.) (1 mCi/ml 37.0 MBq/ml). After 20 min the assays were terminated by heating the reaction mixture at 90° C. for 5 min. The precipitates were removed by centrifuging at 15,000 rpm for 20 min. Ten microliters (≈50,000 cpm) of the supernatant was spotted on activated Avicel TLC plates (Analtech, Newark, Del.). The TLC plates were developed in a solvent system consisting of ethanol:water:ammonia (80:16:4). Quantitation of the spot for L-[$^3$H]-citrulline was performed by a Bioscan System 200 Imaging Scanner. A phosphoimager can also be used for such quantification.

Assays for iNOS in whole cells. Similarly, whole cell iNOS assays using RAW 264.7 cells and bovine chondrocytes have been carried out. Briefly, cells were induced with LPS for 24 hours, scraped from the plate, and washed once with PSS buffer (consisting of NaCl 140 mM; KCl 4.6 mM; CaCl$_2$ 2.0 mM; MgCl$_2$ 1.0 mM; glucose 10.0 mM and Hepes 10.0 mM, pH 7.4). The required number of cells (1–2×10$^6$) were resuspended in 100 µl of PSS spiked with 1 µl (250 nM) of L-[$^3$H]-arginine, and incubated at 37° C. for 10 minutes. Cells were spun down to remove excess of L-[$^3$H]-arginine, resuspended in 30 µl of PSS, and then lysed by repeated freeze-thawing. Debris was removed by centrifuging the cells at 14,000 rpm for 20 minutes; 20 µl of the supernatant was spotted on TLC.

Assay for prostaglandin endoperoxide H synthase-2 (COX-2) in whole cells. Cells were incubated with LPS (1 µg/ml) for 16 h to induce COX-2, exposed to NSAIDs for 1 h and subsequently harvested. The harvested cells were then incubated with radiolabelled arachidonic acid (100,000 cpm, 57 mCi/mM) in 1 ml of Tris HCl (together with 3 µM of cold arachidonic acid) for 10 min. Specific enzyme activity (whole cell assays) was measured by the conversion of $^{14}$C-arachidonic acid to PGE$_2$ after separation by thin-layer chromatography (Vane et al., 1994, supra; Mitchell et al., *Proc. Natl. Acad. Sci. USA* 90, 11693–11697, 1993). Authentic prostaglandin and monohydroxy standards were run in parallel. The transformed products were quantitated by a Bioscan System 200 imaging Scanner.

RESULTS

Effects of NSAIDs on Nitrite Accumulation. Murine macrophage cells (RAW 264.7) were selected for this study because the regulation of iNOS in these cells has been well-characterized, both at the biochemical and molecular level (Nathan et al., *Cell* 78, 915–918, 1994; Stuehr et al., *Proc. Natl. Acad. Sci. USA* 88, 7773–7777, 1991; Xie et al., *J. Biol. Chem.* 269, 4705–4708, 1994). PAW 264.7 cells were activated with 100 ng/ml of LPS to induce iNOS (Stuehr et al., 1991, supra) in the presence and absence of aspirin (1–3 mM), sodium salicylate (2–3 mM) and indomethacin (5–20 µM). The expression and activity of iNOS were monitored by estimation of the stable end-product: nitrites. Table 1 shows a concentration-dependent inhibition of nitrite accumulation in cells stimulated with LPS in the presence of 1–3 mM aspirin. Suprapharmacological concentrations of aspirin (5 and 10 mM) further inhibited nitrite accumulation (by 50% and 80%, respectively) above that observed at 3 mM concentration (data not shown). Sodium salicylate (3 mM) and indomethacin (5 µM) did not significantly inhibit nitrite production (~7% inhibition). Suprapharmacological concentrations of sodium salicylate (5 mM) caused 15±1% inhibition of nitrite accumulation under identical conditions. However, $IC_{50}$ of sodium salicylate with respect to nitrite accumulation was 20 mM, whereas its ability to inhibit fMet-Leu-Phe-induced neutrophil aggregation was 3 mM (data not shown) (Abramson et al., 1985, supra). Although indomethacin is known to be effective therapeutically at 20 µM, the extent to which it inhibited nitrite accumulation was not appreciably greater than that seen with 5 µM. Our results on the effect of indomethacin on nitrite accumulation in RAW 264.7 cells were identical to those observed by Salvemini et al. (1993, supra). Acetaminophen (60–120 µM), an analgesic agent closely related to salicylates, failed to block nitrite production (1±1%) in LPS-stimulated macrophages at therapeutic concentrations. As previously shown by Moncada and co-workers in murine macrophages (J774 cells) (Di Rosa et al., Biochem. Biophys. Res. Comm. 172, 1246–1252, 1990), and as seen in the present study (Table 2), hydrocortisone (5 µM) inhibited endotoxin-induced NO production by >60%.

The capacity of selected drugs to inhibit the specific activity of COX-2 was compared in RAW 264.7 cells exposed to 100 µg/ml of LPS over 16–18 hours of incubation as shown in Table 2. Aspirin (3 mM) and indomethacin (20 µM) each inhibited the specific activity of COX-2 by >75%, while sodium salicylate (3 mM) had no effect. This data indicates that aspirin does not inhibit nitrite production by inhibiting COX, since aspirin shares this effect with indomethacin.

TABLE 1

Effect of NSAIDs on nitrite accumulation and specific activity of iNOS in murine macrophages induced with LPS.

| | Nitrite released | | | Specific activity | | |
|---|---|---|---|---|---|---|
| | Nitrite (µM) | % inhibition | (p value) | pmol/min/mg protein | % inhibition | (p value) |
| Control (uninduced) | 0.5 ± 0.5 | — | — | 11.7 ± 1.5 | — | — |
| LPS-induced | 29.2 ± 6.8 | — | — | 310.0 ± 54.6 | — | — |
| Aspirin (1 mM) | 26.6 ± 4.3 | 10 | (<0.267) | 271.7 ± 17.2 | 12 | (<0.155) |
| Aspirin (2 mM) | 22.9 ± 5.3 | 22 | (<0.071) | 231.3 ± 29.8 | 25 | (<0.046) |
| Aspirin (3 mM) | 20.3 ± 3.9 | 32 | (<0.025) | 162.3 ± 25.9 | 48 | (<0.006) |
| Sodium salicylate (3 mM) | 27.1 ± 8.8 | 7 | (<0.345) | 304.0 ± 48.1 | 2 | (<0.446) |
| Indomethacin (5 µM) | 27.5 ± 7.7 | 7 | (<0.365) | 304.0 ± 39.4 | 2 | (<0.441) |

Murine macrophage cells (RAW 264.7) were incubated with various concentrations of NSAIDs for 2 h followed by addition of 100 ng/ml of LPS. After 16–18 h of incubation, the medium was used to estimate the accumulation of nitrite by the Greiss method (Green et al., Anal Biochem. 12b:12299, 1982). The specific activity of iNOS was determined in cell-free extracts at a given time period as described. The nitrite and specific activity data are representative of mean ± SD value, as determined by student t test, for 10 and 4 independent experiments, respectively. The p values described are compared with LPS-stimulated cells.

TABLE 2

Summary of the action of NSAIDs on expression of iNOS and COX-2.

| | Percent of inhibition of iNOS | | | | | |
|---|---|---|---|---|---|---|
| | at 16 hours | | | | | |
| Modulating agent | nitrite release | specific activity in cell-free extracts | protein expression | mRNA | specific activity in in vitro assay | % inhibition of COX-2 specific activity |
| Aspirin (3 mM) | 32.0 | 47 | ~53 | NS | ~45 (1 mM) | >75 |
| Sodium salicylate (3 mM) | 7.0 | 2 | ~15 | NS | ~1 (1 mM) | NS |
| Indomethacin (5 µm) | 7.0 | 2 | 0 | NS | 0 (5 µM) | >75 |
| Hydrocortisone (5 µm) | 63.0 | ND | ND | ND | ND | ND |
| N-acetylimidazole (1 mM) | ND | ND | ND | ND | ~74 (1 mM) | ND |

The data (expressed as percent inhibition) are compiled from the present study. RAW 264.7 cells were induced with 100 ng/ml of LPS to stimulate iNOS and COX-2 activity. After 16–18 h of incubation, COX-1/COX-2 activity was assayed as described by Mitchell et al. (Proc. Natl. Acad. Sci. USA 90:11693–11697, 1993). COX-1 activity was not detected in these cells, as previously described (Salvemini et al., Proc. Natl. Acad. Sci. USA 90:7240, 1993). The protein expression data are represented as approximate percent inhibition based on the densitometry data from one of the two representative experiments. ND = not done. NS = not significant.

Effect of NSAIDs on the Expression and Catalytic Activity of iNOS. Since nitrite accumulation, which represents the cumulative effect of iNOS expression from induction of the enzyme, does not directly assess the effects of pharmacologic agents (i.e., NSAIDs) on specific enzyme activity, we analyzed these two parameters in tandem.

The specific enzyme activity of iNOS from cells exposed to aspirin in cell-free extracts showed a significant inhibition in activity in a dose-dependent fashion ($IC_{50}$=3 mM). Sodium salicylate and indomethacin did not inhibit the specific activity of iNOS (Table 1).

A Western blot analysis of iNOS protein was carried out in cells treated with 100 µg/ml LPS in the presence and absence of NSAIDs for 16–18 h. The results show a significant decrease in the expression of iNOS in cells treated with aspirin, thus accounting in part for the decrease in the specific activity of iNOS. Aspirin at 10 mM concentration further decreased the expression of iNOS by 69%, as determined by Western blot analysis. Therapeutic concentration of sodium salicylate (2 mM) caused ~15% inhibition of iNOS expression, whereas 5 µM indomethacin showed no effect, as assessed by Western blot analysis. It should be noted that sodium salicylate (2–3 mM) caused a variable (0–35%) inhibition of iNOS expression at therapeutic concentrations in 4 independent experiments. However, increased concentration of sodium salicylate (5 and 20 mM) did not cause increased inhibition of iNOS expression, unlike the increasing effects seen with 10 mM aspirin (~70%). These results are not easily interpreted, but it is assumed that sodium salicylate at lower concentrations interferes with synthesis of the enzyme, whereas at higher concentrations it inhibits the catalytic activity of iNOS. This biphasic effect would account for a decrease in nitrite production without apparent decrements of protein synthesis, as assessed by Western blot analysis.

Previous studies have shown that induction of iNOS and COX-2 are both achieved by LPS in RAW 264.7 cells after 12–16 h (10). Indomethacin (20 µM) inhibited COX-2 activity by >75% but had no effect on iNOS expression in Western blot analysis. Furthermore, since indomethacin had minimal effects on iNOS activity at therapeutic concentrations, COX-2 or its products are unlikely to be regulators of iNOS activity per se, at least in murine macrophages.

Effect of NSAIDs on the Expression of iNOS MRNA. Aspirin may suppress iNOS expression early in the course of enzyme induction, leading to inhibition or delay in the accumulation of nitrites. This assumption is based on the observation that, in macrophages, TGF-β1 suppresses iNOS expression by decreasing MRNA stability and translation and increasing the degradation of iNOS protein in macrophages (Vodovotz et al., *J. Exp. Med.* 178, 605–613, 1993). There was no significant difference in the expression of iNOS mRNA (at 16 h) in cells treated with LPS in the presence or absence of NSAIDS, since the ratios between the expression of iNOS mRNA/β-actin mRNA were either identical or not significantly different from cells stimulated with LPS alone (data not shown). Recent studies by Tetsuka et al. (*Proc. Natl. Acad. Sci. USA* 91, 12168–12172, 1994) have demonstrated that addition of indomethacin enhanced IL-1β-induced steady state level of iNOS mRNA and nitrite production in rat mesangial cells. Hence, our studies indicate that the effect of indomethacin may be different in different cell types. Kopp and Ghosh (*Science* 265, 956–959, 1994) showed that aspirin (3 mM) or sodium salicylate (5 mM) inhibit NF-κB-dependent transcription, using sensitive assays based on plasmids containing two IgK-κB sites driving a luciferase reporter gene. It should be noted that, in the same studies, the same concentrations of aspirin and sodium salicylate had no significant effect on NF-κB activation, judged by gel shift assays. Nathan and co-workers have shown that NF-κB expression is one of the integral components of iNOS transcription/expression (Xie et al., 1994, supra), which can be inhibited by an NF-κB inhibitor, pyrrolidine dithiocarbamate at 30 µM. Our studies indicate that 3 mM aspirin is probably not sufficient to block the transcription of the iNOS gene, as observed with 30 µM of pyrrolidine dithiocarbamate, which blocked >90% of nitrite accumulation in our studies (data not shown). Furthermore, the lack of significant effect of aspirin and sodium salicylate on iNOS MRNA expression, and the differential effect of aspirin and sodium salicylate on iNOS expression, support the above notion that aspirin and sodium salicylate have no significant effect on the expression of iNOS at the gene level, at least in murine macrophages activated with LPS in vitro. This further reinforces the notion that the mechanism of action of aspirin in inhibiting iNOS expression is due to its interference in translational/post-translational modification of the enzyme and/or inhibiting the catalytic activity of iNOS.

Effect of NSAIDs on the Catalytic Activity of iNOS in Cell-Free Extracts. The effects of aspirin, sodium salicylate and indomethacin was examined in in vitro iNOS enzyme assays. RAW 264.7 cells were incubated overnight with LPS to induce iNOS. Cell-free extracts were prepared from these cells and used as a source of iNOS. These enzyme extracts were preincubated with NSAIDs for 20 min before initiating the enzyme reactions as described above. Aspirin at 0.1 and 1 mM concentration inhibited the conversion of L-[$^3$H]H-arginine to L-[$^3$H]-citrulline in cell-free extracts by 10–12% and 45–68%, respectively (FIGS. 1 and 2), whereas no significant differences (7%) were observed in extracts treated with 1 mM of sodium salicylate. Similarly, 5 µM indomethacin or equivalent volume of alcohol had no effect (FIG. 1). These studies demonstrated that aspirin, but not sodium salicylate or indomethacin, directly interfered with the catalytic activity of iNOS by acetylating an important functional component of the enzyme or its co-factors. However, since sodium salicylate at therapeutic (2 mM) and suprapharmacological (5 and 20 mM) concentrations inhibits accumulation of nitrites (by 7%, 15% and 50%, respectively) and has only minimal and insignificant effect on the expression of the iNOS protein, the possibility of sodium salicylate interfering with iNOS catalytic activity at suprapharmacological concentrations cannot be ruled out.

Effect of N-acetylimidazole (NAI) on the Catalytic Activity of iNOS in Cell-Free Extracts. Unlike aspirin, which acetylates Ser$^{530}$ of COX and inactivates the cyclooxygenase and not the peroxidase activity (Lecomte et al., *J. Biol. Chem.* 269, 13207–13215, 1994), NAI acetylates and inhibits both the cyclooxygenase and the peroxidase activity of COX (Wells et al., *Biochemistry* 31, 9520–9525, 1992). The effect of NAI on the catalytic activity of iNOS in cell-free extracts was tested and compared with equivalent amounts of aspirin in the same experiment. FIG. 2 shows the dose-dependent inhibition of iNOS by NAI and aspirin. In contrast to aspirin, which does not seem to inhibit the iNOS activity significantly (10–12%) at 0.1 mM (FIGS. 2 and 3), NAI at similar concentrations inhibited ~45% of iNOS activity. However, at 1 mM, aspirin and NAI inhibited the catalytic activity of iNOS by 45% and 74%, respectively. These experiments further demonstrate that acetylation of iNOS inactivates its catalytic activity, and that the potency of NAI is relatively greater than that of aspirin. Similar results were obtained using whole cell assay of iNOS (data not shown) NAI, which is commonly used for acetylation of tyrosine hydroxyl groups (Riordan et al., *Biochemistry* 4, 1758–1765, 1965; Riordan et al., *Methods Enzymol.* 25B, 494–499, 1972; Riordan et al., *Methods Enzymol.* 25B, 500–506, 1972), acetylates protein residues at rates proportional to their nucleophilicity and accessibility (Wells et al., 1992, supra; Riordan et al., 1965, supra).

These observations may explain the differential potency of aspirin and sodium salicylate. Aspirin inhibits iNOS by effects on both synthesis of the iNOS protein and on the catalytic activity of the enzyme, by acetylation of the enzyme and/or an essential co-factor, whereas indomethacin and sodium salicylate (which weakly inhibits iNOS protein expression) have no significant effect on the catalytic activity of iNOS. However, the possibility that aspirin interferes in the biosynthesis of other crucial co-factors cannot be excluded (Schmidt et al., *Cell* 78, 919–925, 1994; Marletta, *Cell* 78, 927–930, 1994).

Unstimulated and LPS stimulated murine macrophage (RAW 264.7) cells were incubated with radiolabelled aspirin (acetyl group labelled) as described by Lecomte et al. (*J. Biol. Chem.* 269:13207–13215, 1994). After 30 minutes, the extracts were run on an SDS-PAGE gel and analyzed by phosphoimager. The data show radiolabelling or proteins in the region of 133 kD where iNOS was observed to migrate in the same filter paper (Western blot, probed with α-iNOS antibodies). The intensity of label ($^{14}C$) is increased, where iNOS synthesis was induced by LPS.

Consequently, incubation of iNOS with radiolabelled aspirin shows acetylation of iNOS, indicating that inhibition of iNOS was due to direct acetylation of iNOS and not due to its effect on a co-factor that influences iNOS enzymatic activity. However, the possibility that inhibition of iNOS catalytic activity may be due to acetylation of cofactors/precursors of iNOS has not been ruled out. These results show a new mechanism of action of aspirin on iNOS expression, not previously described.

Figure 5A:
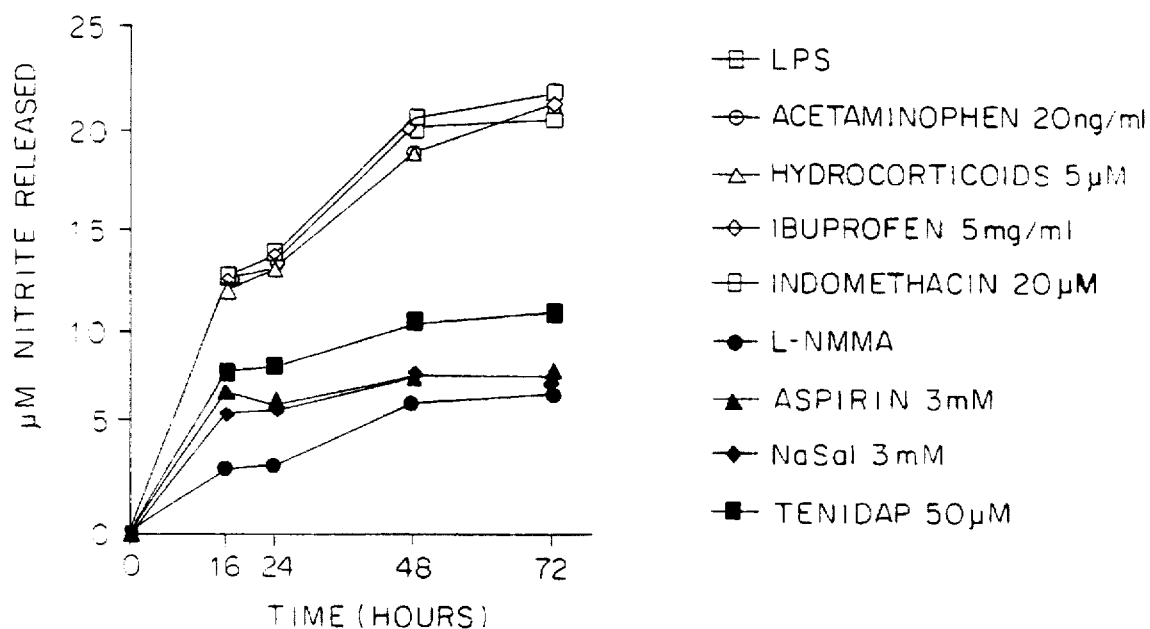
Figure 5B:
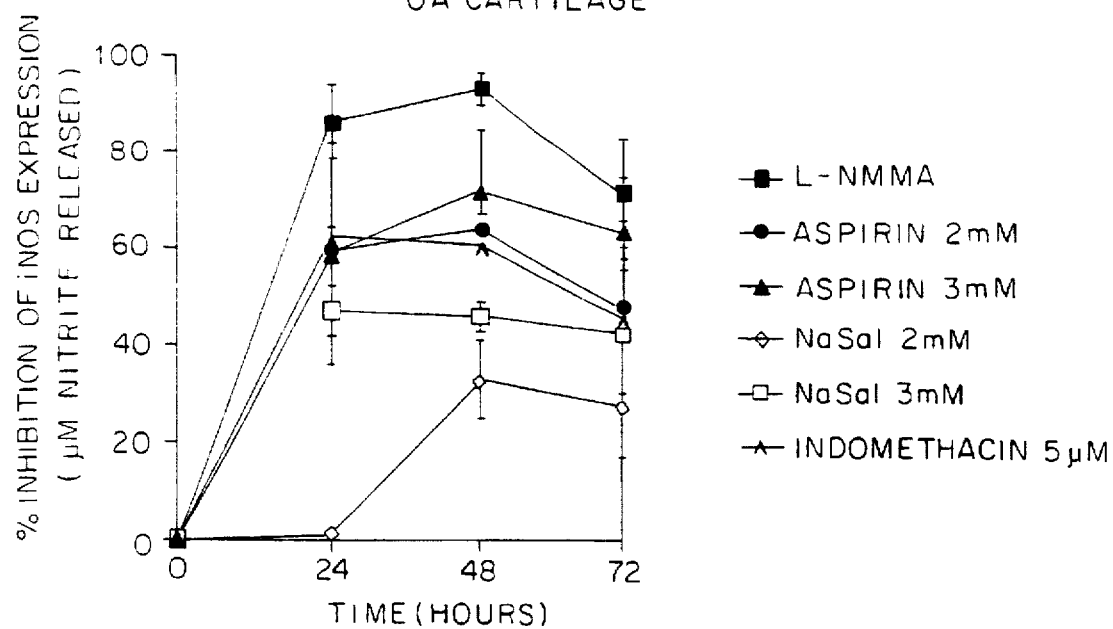

Addition of NSAIDs to rat chondrosarcomas (Choi et al., *Proc. Natl. Acad. Sci. USA* 68:877–879, 1971) 1 h prior to addition of cytokines showed that aspirin inhibits iNOS expression by ~57%, sodium salicylate by ~55%, tenidap (Pfizer) by ~50%, and L-NMMA by ~65% at 72 h (FIG. 5A). There was no significant effect on iNOS expression in cells incubated with indomethacin, acetaminophen, hydrocortisone and ibuprofen (FIG. 5A). Insensitivity of rabbit chondrocyte iNOS to glucocorticoids has been reported previously (Palmer et al., 1992, supra; Stefanovic-Racic et al., *Arthritis Rheum.* 37 (9 Suppl.):S386, 1994b). Similarly, experiments shown in FIG. 5B show that NSAIDs [aspirin>indomethacin>sodium salicylate] inhibit the spontaneous accumulation of nitrite in OA cartilage. It should be noted that the inhibitory effect of indomethacin (on NOS expression) as seen for the human OA-NOS was not significant in rat chondrosarcomas or murine macrophages expressing iNOS, although indomethacin was added after the induction of NOS in human OA cartilage. Thus indomethacin, like aspirin and sodium salicylate, can reverse the effect of NOS in OA cartilage. These results indicate that the sensitivity of chondrocyte NOS to various NSAIDs is greater than that demonstrated for the murine iNOS, and it may also vary among chondrocytes from different species. Furthermore, experiments conducted with OA cartilage (which already has upregulated NOS prior to addition of NSAIDs) indicate that NSAIDs can partially reverse the expression of NOS in human chondrocytes.

In the studies presented as Example 1, the effects of aspirin were not observed to be restricted to murine macrophages. Slices of human osteoarthritic cartilage, in contrast to normal human cartilage, showed upregulated NOS and accumulated >70 µM of nitrites in the medium, concentrations sufficient to provoke tissue damage. Addition of 2 mM of aspirin suppressed accumulation of nitrites by at least 50% in ex vivo experiments, thus indicating that human chondrocyte NOS (which is similar to murine iNOS) is sensitive to aspirin, and may also be sensitive to other NSAIDs.

It is clear from these experiments that aspirin does not inhibit iNOS expression completely at the therapeutic concentrations selected in this study. However, it should be noted that partial suppression of iNOS may be sufficient to inhibit an inflammatory response. This assumption is supported by studies in animal models, where partial inhibition of NOS by NOS inhibitors in rats with induced adjuvant arthritis was sufficient to reduce paw swelling (indicating reduction in inflammation) without significantly affecting the elevated excretion of nitrites in the urine (Stefanovic-Racic et al., *Arthritis Rheum.* 37, 1062–1069, 1994). Thus small reductions in NO levels may have profound effects on the process of inflammation, and aspirin-like agents which do not completely inhibit iNOS/OA-NOS expression at therapeutic concentrations may still be good candidates for pharmaceutical intervention to modulate iNOS/OA-NOS. These data also show that at equivalent therapeutic levels, salicylates and indomethacin have divergent effects on iNOS. Such observations are consistent with previous studies which have shown important differences among NSAIDs with regard to their capacity to inhibit neutrophil function (Abramson et al., 1985, supra), COX-2 activity (Mitchell et al., 1993, supra), NF-κB activation (Kopp et al., 1994, supra), and neurogenic inflammation (Abramson, *Curr. Opin. Rheumatology* 4, 295–300, 1992).

In summary, it is concluded that the inhibition of iNOS/OA-NOS expression/function represents a novel mechanism of action of aspirin-like drugs and may explain individual differences in response to NSAIDs in patients with inflammatory diseases.

EXAMPLE 2

Expression and Regulation of Nitric Oxide Synthase in Human Osteoarthritis-Affected Chondrocytes Studies involving animal arthritis models and analysis of human synovial fluids have implicated NO in the pathogenesis of arthritis. Induction of arthritis in rodent models resulted in increased production of nitrites and nitrates prior to the onset of clinical symptoms. The appearance of articular symptoms and joint degeneration could be inhibited by administration of a NOS inhibitor (McCartney-Francis et al., 1993, supra). Increased concentrations of nitrites were reported in human synovial fluid from RA and OA patients, suggesting that NO may be a mediator of inflammation in both diseases (Farrell et al., *Ann. Rheum. Dis.* 51:1219–1222, 1992).

In this example it is reported that: (a) the $M_r$ of an "osteoarthritis-affected NOS" (OA-NOS) is similar to ncNOS and distinct from other iNOS, but shares regulatory properties with iNOS; (b) chondrocytes from human OA-affected articular cartilage have NOS that is complexed with calmodulin and can synthesize NO; (c) the prolonged (72 h) accumulation of NO by OA cartilage in ex vivo experiments is indicative of "NO stimulating factor(s)" within the cartilage, and this phenomenon is sensitive to inhibitors of protein synthesis and of the transcription factor NF-κB.

In this example, the following materials and methods were used:

Reagents and Cell Lines. A macrophage-like cell line, RAW 264.7, was obtained from ATCC (Rockville, Md.). Monoclonal antibodies (mAb) to murine ecNOS (cat.# N30020) and affinity purified polyclonal rabbit antibodies to ncNOS (cat.# N31030) were obtained from Transduction Laboratories (Lexington, Ky.), polyclonal rabbit antibodies to iNOS (cat.# PA3-030) were obtained from Affinity Bioreagents, Inc. (Neshanic Station, N.J.) anti-calmodulin antibodies from UBI (Lake Placid, N.Y.), protease inhibitors, cycloheximide, pyrrolidine dithiocarbamate (PDTC), aminoguanidine and LPS from Sigma (St. Louis, Mo.), human IL-1β and TNF-α from Fisher Scientific (Springfield, N.J.), and L-NMMA from Chem-Biochem Research Inc. (Salt Lake City, Utah).

Isolation of Bovine Chondrocytes. Bovine cartilage was washed after removing the perichondrium, cut into small pieces, and digested with pronase (0.1%) in PBS for 30 min, followed by digestion with collagenase P (0.1%) for 12–16 h in F-12 medium. Cells were then washed and resuspended in the respective media for experiments.

Extraction of Human Chondrocyte NOS and Western Blotting. Slices from articular cartilage affected by OA were frozen at −70° C., milled to fine particulate in liquid nitrogen, and sequentially extracted (10 ml/gram wet weight tissue) with neutral salt buffer (Tris HCl:saline) containing protease inhibitors (1 mM PMSF, 2 mM N-ethylmaleimide, and 0.025 mg/ml leupeptin), followed with the same buffer containing 10 mM EDTA, with 4 M guanidine-HCl, and then with a detergent buffer containing 10% SDS with protease inhibitors. Samples were run on 9% or 4–15% gradient SDS-PAGE gels under non-reducing conditions, transferred to nitrocellulose, and Western blotted with α-iNOS/α-ncNOS or α-calmodulin mAb (Cho et al., *J. Exp. Med.* 176:599–604, 1992). Bound antibody was detected by a secondary antibody conjugated with horseradish peroxidase, and developed using the ECL Western blotting system (Amersham, Arlington Heights, Ill.) on Kodak Xomatic X-ray film.

Isolation of Recombinant Human Hepatocyte iNOS. Human hepatocyte iNOS was obtained from NIH 3T3 fibroblasts transduced with a retrovirus carrying the human hepatocyte iNOS CDNA.

Results and Discussion

The studies in this example were initiated by standardizing conditions of extracting NOS directly from OA-affected articular cartilage prior to cell fractionation. Sequential extraction with various buffers showed that human chondrocyte NOS is a non-membrane bound cytosolic enzyme. Approximately 90% of OA-NOS was present in the neutral salt fraction, ~10% was seen in the EDTA-containing buffer, and no OA-NOS was detected by Western blot analysis in either the 4M guanidine HCl extract or detergent extract.

To further evaluate the expression of OA-NOS, equal amounts of extracts from OA-affected and non-arthritic articular cartilage were subjected to Western blot analysis and reacted against anti-murine iNOS antibodies. The OA cartilage was obtained from OA patients who underwent knee replacement surgery and were free of steroidal/non-steroidal anti-inflammatory drugs for at least two weeks prior to surgery and non-arthritic normal knee cartilage was obtained from the Musculoskeletal Transplant Foundation within 24 hours of death. All 12 patients with OA demonstrated expression of NOS, whereas no NOS was detected from non-arthritic control cartilage. The OA-NOS detected in all 12 patients had the same $M_r$, which was distinct from murine iNOS.

The $M_r$ of the human OA-iNOS was compared with the murine macrophage iNOS, human hepatocyte iNOS, and rat ncNOS and human endothelial cell NOS (ecNOS). The α-ncNOS antibodies used to detect human OA-NOS were raised by Transduction Labs from peptide sequence 1095 to 1289 for ncNOS. The polyclonal α-iNOS and the affinity purified polyclonal α-ncNOS antibodies did not bind to ecNOS. Western blot analysis shows that the 155 kD human OA-NOS, which co-migrated with murine IgG, is distinct in size from the iNOS from human hepatocytes (native and transfected), human B cells and murine macrophages (Xie et al., *Science.* 256:225–228, 1992; Mannick et al., *Cell.* 79:1137–1146, 1994), which are 133 kD. The molecular weight of all OA-chondrocyte iNOS tested was 155 kD, a size clearly different from previously reported iNOS. A similar molecular weight NOS has also been identified in RA-affected articular cartilage.

The α-iNOS polyclonal antibody cross-reacts with iNOS from various species, including bovine chondrocytes. However, it does not cross-react with OA-NOS. It should be noted that the polyclonal Ab raised against the ncNOS is very specific for ncNOS. The polyclonal α-ncNOS Ab binds to rat ncNOS and OA-NOS, but not to ecNOS, human hepatocyte or murine macrophage iNOS. The α-iNOS polyclonal antibody, however, binds to murine and hepatocyte iNOS, but not to OA-NOS or ncNOC (neuronal or brain NOS). Furthermore, the α-ncNOS polyclonal antibody binds to NOS from brain extracts and OA cartilage, but not from murine macrophages and human hepatocyte extracts.

To further characterize the nature of OA-NOS, preliminary studies with anti-calmodulin antibodies were conducted which indicated that both the 155 kD OA-NOS and the 133 kD human hepatocyte iNOS are complexed with calmodulin, a characteristic feature of iNOS, as previously shown for murine iNOS (Cho et al., 1992, supra). These results also indicate that the presence of calmodulin in OA-NOS may not necessarily account for the increase (~17 kD) in the $M_4$ of OA-NOS. EDTA or EGTA markedly reduces the human iNOS activity in crude lysates from transfected kidney 293 cells (Geller et al., *Proc. Natl. Acad. Sci. USA.* 90:3491–3495, 1993) or native human hepatocyte iNOS, suggesting that calmodulin binding to human iNOS may be dependent on a low threshold level of calcium. Although the mRNA for iNOS has been reported to be 4.4 kb for human chondrocytes, hepatocytes and murine macrophages, with <1% difference in cDNA sequence, our results indicate that the translated human OA-NOS has a larger molecular weight (by at least 17 kD) than predicted from the iNOS cDNA sequence.

Hence, the results obtained indicate that OA-NOS is structurally similar to ncNOS based on its size and reactivity to specific α-ncNOS antibodies which do not recognize iNOS from human hepatocytes and rodent macrophages (Table 3), in spite of the marked homology in the region from which the α-ncNOS antibodies were raised. The biochemical characteristics in Table 3 indicate that OA-NOS has biochemical properties similar to iNOS but structural properties similar to ncNOS.

TABLE 3

Properties of OA-NOS in comparison with iNOS and ncNOS.

| | iNOS | OA-NOS | ncNOS |
|---|---|---|---|
| STRUCTURAL PROPERTIES: | | | |
| Size (kD) | 133 | 155–160 | 155–160 |
| Reactivity to α-ncNOS polyclonal antibody | – | + | + |
| Reactivity to α-iNOS polyclonal antibody | + | – | – |
| Calmodulin binding | + | + | – |
| BIOCHEMICAL PROPERTIES: | | | |
| Sensitivity to: | | | |
| cycloheximide (1–2 µg/ml) | + | + | – |
| TGF-β (2.5 ng/ml) | + | – | – |
| hydrocortisone (5–10 µm) | +/–* | – | – |
| aspirin (1–3 mM) | + | + | ? |
| indomethacin (5–10 µM) | – | + | ? |
| sodium salicylate (1–3 mM) | – | + | ? |
| cyclosporin (5 µg/ml) | + | + | ? |
| PDTC (30 µM) | +/–** | + | – |
| aminoguanidine (200 µM) | + | + | – |
| L-NMMA (500 µM) | + | + | – |
| Inducible by cytokines and endotoxin*** | + | + | – |

*+ murine macrophage, – human chondrocytes;
**+ murine macrophage, – human macrophage
***IL-1 (1 ng/ml) + TNF (1 ng/ml) + LPS (100 µg/ml)

Figure 3A:
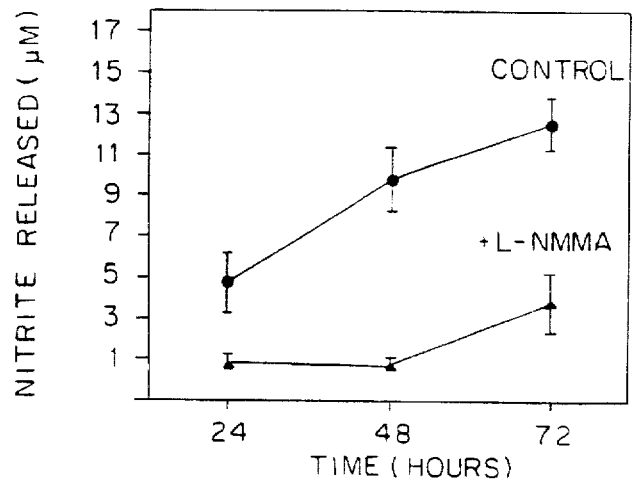
FIG. 3A shows the release of nitrite by OA-affected articular cartilage in ex vivo conditions. Knee articular cartilage from OA patients was cut into 3 mm discs (12±0.04 mg/disc) immediately after surgery and placed in Hams-F-12 media with 10 mM Hepes pH 7.4, together with gentamicin and fungizone (Gibco BRL, Gaithersburg, Md.). Two discs were placed in 1 ml of medium in the presence and absence (CONTROL) of 500 µM L-NMMA. Samples obtained at various time intervals were assayed for nitrite by modified Greiss reaction (17) using an ELISA reader. Data are expressed as µM nitrite released ± standard deviation (n=4–7). The p values between the CONTROL and L-NMMA treated cultures were: 24 h=0.034; 48 h=0.010; 72 h=0.006.

Organ culture of OA-affected cartilage was set up to assess the biological activity of OA-NOS. OA cartilage incubated with serum-free medium demonstrated a steady accumulation of nitrites up to 72 h (FIG. 3), indicating that production of nitrites is "spontaneously" and constantly stimulated in OA cartilage, or released by a constitutive NOS similar to ncNOS. This constant stimulation of nitrite production was inhibited by L-NMMA (FIG. 3a). The absence of NOS activity in normal resting chondrocytes from various species, including human chondrocytes, has also been reported by other investigators, thus excluding the expression of iNOS or OA-NOS in normal resting human chondrocytes. Previous attempts (Palmer et al., Biochem. Biophys. Res. Commun. 193:398–405, 1993) to amplify NOS by RT-PCR from resting chondrocytes using conserved (NADPH regions) degenerate oligonucleotide primers did not yield the expected signal, whereas the same RNA preparations yielded the β-actin bands using appropriate primers. Furthermore, these conserved degenerate primers could amplify a partial iNOS sequence from IL-1-stimulated chondrocytes. These experiments exclude the possibility of a cNOS in resting chondrocytes (Palmer et al., 1993, supra).

However, it is quite conceivable that the expression of OA-NOS is triggered only under pathological conditions such as OA. Tubular epithelial cells are now known to constitutively generate NO and an iNOS (stimulated by cytokines) which produces far greater quantities of NO also exists in these cells.

Figure 3B:
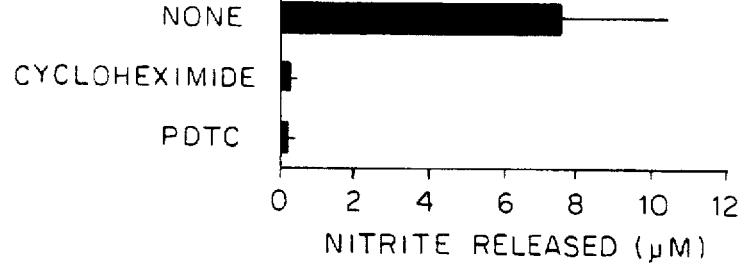
FIG. 3B shows release of nitrite by OA cartilage in ex vivo conditions after 24 h in the presence and absence (CONTROL) of cycloheximide (35 µM) and PDTC (30 µM). OA cartilage was incubated with LPS (100 µg/ml), IL-1β (1 ng/ml) and TNF-α (1 ng/ml) in the presence and absence of equivalent amounts of cycloheximide or PDTC. Data are expressed as µM nitrite released ± standard deviation (n=4). The p value between the CONTROL versus cycloheximide- and PDTC-treated cultures was <0.035; p values between cytokine-/endotoxin-treated cultures, versus cycloheximide/PDTC, were <0.013.

The expression of OA-NOS was evaluated for its sensitivity to cycloheximide and NF-κB inhibitor PDTC. Addition of 3.5 µM and 17.5 µM of cycloheximide to OA cartilage showed >90% inhibition of nitrite accumulation as compared to controls after 24 h. The data in FIG. 3b show a representative experiment in which addition of cytokines and endotoxin augmented the release of nitrite in the medium. Nitrite accumulation was significantly blocked by >90% in both the cytokine- and endotoxin-induced cartilage and control cartilage in the presence of cycloheximide or PDTC, thus indicating that the OA-affected chondrocyte NOS activity is sensitive to cycloheximide and PDTC with respect to production of nitrites in ex vivo cultures. NF-κB induction/expression and de novo protein synthesis have previously been shown to be prerequisites for iNOS expression in murine macrophages (Xie et al., J. Biol. Chem. 269:4705–4708, 1994) and human chondrocytes (Palmer et al., 1993, supra). The present data indicate that inhibition by PDTC/cycloheximide of nitrite accumulation in OA cartilage may be due to inhibition of de novo protein synthesis of NOS itself, co-factors involved in the regulation of NOS, or both. Incubation of OA-affected articular cartilage, either in basal medium alone or supplemented with BSA had insignificant impact on the release of nitrites. It should be noted that the NOS found in rat chondrosarcomas is different from humans OA-NOS showing that similar types of cells have different kinds of NOS. The iNOS discovered in rat chondrosarcoma tumor cells is a 133 kD iNOS whereas the OA-NOS from human cartilage has properties similar to iNOS and ncNOS. The difference between rat chondrosarcoma iNOS and human OA-NOS is also reflected in the individual sensitivities to NSAIDs tested in FIGS. 5A and 5B. In similar and parallel experiments using normal adult bovine articular cartilage, or murine RAW 264.7 cells, no detectable amounts (>1 µM) of nitrites were observed after 48 h, indicating that the medium used in these experiments was devoid of any stimulating agent that may have contributed to the upregulation of NOS in OA cartilage on day 2 and 3 in the ex vivo experiments. As expected, addition of LPS (100 ng and 100 µg/ml), showed an accumulation of nitrites in the medium after 20 or 48 h in both murine RAW 264.7 cells and bovine articular cartilage, respectively.

These studies also indicate that a PDTC/ cycloheximide-sensitive "NO stimulating factor(s)" may be present within the OA cartilage, because these organ cultures were devoid of all other tissues except articular cartilage. Potential stimulators of OA-NOS may be one or a combination of the following manifestations: a) autocrine cytokine(s)/growth factor(s) produced by chondrocytes in OA cartilage; b) cell surface receptor [similar to those seen with glutamate receptors in the brain and CD53 on macrophages (Culcasi et al., J. Biol. Chem. 269:12589, 1994; Bosca et al., J. Exp. Med. 179:1119–1126, 1994)] present on chondrocytes that may be triggered by the matrix components; c) diffusion of soluble (paracrine) factors into the cartilage in vivo from other cellular sources of the intra-articular region (e.g., endothelial cells, lining of the synovial capillaries, local inflammatory cells, and/or synovial fibroblasts); d) abnormal mechanical forces seen by the chondrocytes in the 3-dimensional architecture; or e) a change in chondrocyte-matrix interactions which have been altered by the degraded osteoarthritic extracellular matrix and/or a change in chondrocyte integrin receptor profile (Woods et al., Arthritis Rheum. 37:537–544, 1994).

Figures 4A, 4B, 4C:
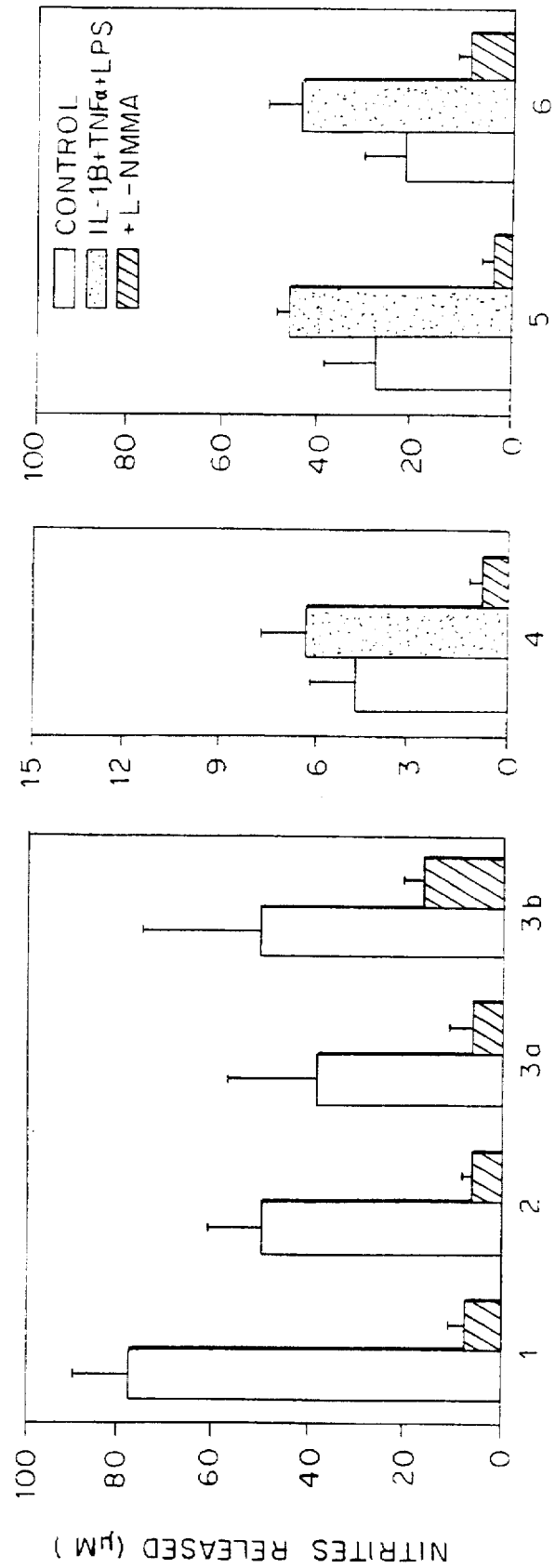
FIG. 4A shows release of nitrite by OA cartilage in ex vivo conditions after 48 h. Knee articular cartilage from 3 OA patients was cut into 1 mm discs; 4–6 discs were placed in organ culture in 2 ml medium in the presence and absence (CONTROL) of 500 µM L-NMMA. 3a and 3b were samples obtained from left and right knees of the same patient. Data are expressed as µM nitrite released±standard deviation (n=4). The p values between CONTROL and L-NMMA treated cultures were: 1=0.013; 2=0.002; 3a=0.066; 3b=0.048.
FIG. 4B shows release of nitrite by OA cartilage in ex vivo conditions after 24 h in presence and absence of LPS (100 µg/ml), IL-1β (1 ng/ml) and TNF-α (1 ng/ml). Knee articular cartilage from 1 OA patient was cut into 1 mm discs; 3–4 discs were placed in organ culture in 2 ml medium in the presence and absence (CONTROL) of 500 µM L-NMMA. One set of cultures was incubated with LPS, IL-1µ and TNF-α. Data are expressed as µM nitrite released±standard deviation (n=7). The p value between CONTROL and L-NMMA treated cultures was 0.034; p value between CONTROL versus LPS, IL-1β and TNF-α treated cultures was 0.005.
FIG. 4C shows release of nitrite by OA cartilage in ex vivo conditions after 48 h in presence and absence of LPS (100 µg/ml), IL-1β (1 ng/ml) and TNF-α (1 ng/ml). Knee articular cartilage from 2 OA patients was cut into 1 mm discs; 3–4 discs were placed in organ culture in 2 ml medium in the presence and absence (CONTROL) of 500 µM L-NMMA. Each set of cultures was also incubated with LPS, IL-1β and TNF-α. Data are expressed as µM nitrite released±standard deviation (n=4–7). The p values between CONTROL and L-NMMA treated cultures were: 5=0.057; 6=0.099. The p values between CONTROL versus LPS, IL-1β and TNF-α treated cultures were: 5=0.088; 6=0.013.

Additional experiments with OA cartilage in organ cultures were carried out and it was found that ~50–100 mg cartilage released ~40–80 µM of nitrites after 48 h, which could be inhibited by L-NMMA (FIG. 4A) or aminoguanidine (not shown). Interestingly, in a single case in which cartilage was obtained from both knees, similar levels of nitrite were observed (FIG. 4A, patient sample No. 3a and 3b). Exposure of the OA cartilage in vitro to pharmacological concentrations of IL-1β and TNF-α and a near-lethal dosage (100 µg/ml) of endotoxin for 24 and 48 h resulted in an increase in NO production (FIGS. 4B and 4C), suggesting that OA-affected chondrocytes generate concentrations of NO that have been associated with degradation of articular cartilage (Farrell et al., 1992, supra). Furthermore, human chondrocytes exposed to exogenous NO, or cytokines and endotoxin (at concentrations used in this study), have demonstrated inhibition of growth, chemotactic responses to growth factors, proteoglycan synthesis and apoptosis (Farrell et al., 1992, supra; Taskiran et al., *Biochem. Biophys. Res. Comm.* 200:142–148, 1994, Blanco et al., *Arthritis Rheum.* 37(Suppl.):S294, 1994). Analysis of synovial fluids from RA and OA patients demonstrated mean nitrite levels of 0.91 µM and 0.34 µM, respectively, whereas control serum background levels were 0.14 µM (Farrell et al., 1992, supra).

These studies further indicate that the biochemical and regulatory properties of OA-NOS are similar to iNOS, because a) its expression is blocked by inhibitors such as cycloheximide, PDTC (blocks murine iNOS but not human iNOS), aminoguanidine and L-NMMA, aspirin and cyclosporin; b) it probably does not need the recruitment of calmodulin for its activity; and c) the production of NOS can be augmented by addition of cytokines and endotoxin (Table 3), which is also sensitive to inhibitors of protein synthesis. However, unlike iNOS, OA-NOS is insensitive to TGF-β and hydrocortisone but is inhibited by indomethacin and sodium salicylate. It should be noted that Moncada and co-workers had proposed that the human chondrocyte iNOS may be different because of its lack of sensitivity to dexamethasone and hydrocortisone that abolishes NOS expression in murine macrophages, endothelial cells and smooth muscles (Palmer et al., 1993, supra; Farrell et al., 1992, supra). Furthermore, unlike hepatocyte iNOS, addition of EGTA to human chondrocyte NOS had no effect on enzyme activity in cell-free extracts (Palmer et al., 1993, supra).

In summary, articular chondrocytes from OA-affected human knees exhibit and express a unique soluble NOS that spontaneously produces NO and that is sensitive to cycloheximide/PDTC as demonstrated by the accumulation of nitrites from organ culture. This enzyme shares structural and regulatory properties of ncNOS and iNOS. Articular chondrocytes are therefore a source of increased levels of intra-articular NO which have been reported in OA patients (Farrell et al., 1992, supra). Our data further support the notion that NO, a known inflammatory component, may exert dysfunction in chondrocytes and thus may be one of the key mediators in the pathogenesis of OA.

Furthermore, high levels of PGE$_2$ (~2900 ng/ml), a product of COX2, were found in cartilage in ex vivo cultures of OA, indicating that inducible COX2 activity, known to be involved in inflammatory conditions, is also present at high levels. Since OA is considered in the art as a non-inflammatory disease, the high levels of PGE$_2$ found to be present in OA cartilage has never been reported. This discovery indicates that COX-2 is induced in OA cartilage and that, besides NO, another inflammatory component (PGE$_2$) similar to NO is present in OA cartilage. PGE$_2$ is expected in RA, a known inflammatory condition, but not in OA.

EXAMPLE 3

Cloning and expression of OA-NOS

In this example, the following methods and materials are to be used.

Purification of human OA-NOS. Cartilage is to be collected from OA-affected patients undergoing knee replacement surgery and the OA-NOS will be extracted as described in Example 2. Briefly, slices from articular cartilage affected by osteoarthritis will be frozen at −70° C., milled to fine a particulate in liquid nitrogen, and sequentially extracted (10 ml/gram wet tissue) with neutral salt buffer (Tris HCl:saline) containing protease inhibitors (1 mM phenylmethylsulfonyl fluoride, 2 mM N-ethylmalemide, and 0.025 mg/ml leupeptin). This extract will be loaded onto an α-iNOS mAb-sepharose 4B column (the α-iNOS antibody has been shown to bind to OA-NOS in Example 2). The column will be washed with buffer and detergents, and the OA-NOS will be isolated with glycine-HCl (pH 2–3). The fractions will be neutralized, concentrated, run on an 4–15% gradient SDS-PAGE gel under non-reducing conditions, transferred to nitrocellulose, and Western blotted with α-iNOS/α-ncNOS or α-calmodulin mAb (Stuehr et al., *Proc. Natl. Acad. Sci. USA* 88:7773, 1991) to verify the identity of the protein.

Partial amino acid sequencing of human OA-NOS. The purified OA-NOS will be sequenced to verify its identity and will also be used to design primers to clone the cDNA by RT-PCR. The purified OA-NOS will be subject to immobilized V-8 protease cleavage and run on an 5–20%, gradient SDS-PAGE gel (Cleveland et al., 1977). The peptide will be transferred to a PVDF (polyvinylidene difluoride) membrane as described by Matsudaira (*J. Biol. Chem.* 262:10035–10038, 1987) and amino acid sequenced.

Preparation of antibodies. Antiserum will be raised by injecting two rabbits with 100 µg of OA-NOS emulsified with Freund's complete adjuvant, followed by two booster injections of incomplete Freund's adjuvant containing 20–60 µg of OA-NOS. The antiserum will be monitored at different time periods (1–4 weeks) after the boost for its reactivity to the purified NOS in ELISA. The total Ig fraction of the antiserum will be purified by protein G. Furthermore, draining lymph node or spleen cells from the appropriate antibody-producing Balb/c mice will be fused with SP2/O-Ag14 HAT-sensitive non-producer myeloma cells, for preparing monoclonal antibodies to NOS. Hybridoma SNs will be screened to assess NOS binding activity in ELISA. Prior to cloning the product of expanded hybridomas, the antibodies will be examined for their ability to immunoprecipitate purified radiolabeled NOS.

The antibodies prepared from OA-NOS will be absorbed against iNOS/ncNOS to remove any cross-reactivity to these NOS isoforms, and specific α-OA-NOS antibodies will be ascertained. Similarly, the hybridomas will be screened for only α-OA-NOS specific Abs. This probe (antibody) will then be used to clone the full-length CDNA by the 5' and 3' RACE (Rapid Amplification of CDNA Ends) protocol (kits) as described by BRL (Grant Island, N.Y.).

cDNA cloning. A) Recently, human iNOS-specific primers were used in cDNA cloning. The sense and antisense oligonucleotides for two iNOS fragments representing the 5' and 3' ends of the enzyme were: (a) 5' ACG GAG AAG CTT AGA TCT GGA GCA GAA GTG 3' (SEQ. ID NO: 1) and 5' CTG CAG GTT GGA CCA CTG GAT CCT GCC GAT 3' (SEQ ID NO: 2), which amplified a 640 bp fragment representing the 5' end of the CDNA; and (b) 5' CGG TGC TGT ATT TCC TTA CGA GGC GAA GAA GG 3' (SEQ ID NO: 3) and 5' GGT GCT GCT TGT TAG GAG GTC AAG TAA AGG GC 3' (SEQ ID NO: 4), which amplified a 258 bp fragment from the 3' end of the CDNA. These primers will be used to amplify and clone the cDNA for OA-NOS by RT-PCR.

Since the OA-NOS demonstrates properties similar to iNOS, these primers are likely to amplify the OA-NOS.

These strategies will facilitate amplification of the OA-NOS cDNA directly by RT-PCR.

B) A second alternative strategy will be to prepare cDNA libraries from the human OA cartilage (Malech et al., *J. Clin. Invest.* 260:2509–2514, 1989). RNA will be isolated from these cells by a modification of GuSCN-CsCl gradient method of Chirgwin et al., (*Biochemistry* 18:5294–5299, 1979), modified by Aruffo and Seed (*Proc. Natl. Acad. Sci. USA*, 1987), in which the LiCl is added to the GuSCN. Poly A plus mRNA will be isolated using oligo-dT cellulose affinity columns (Invitrogen Corp., San Diego, Calif.). A unidirectional cDNA library will be constructed in a λ Zap II vector (Stratagene, La Jolla, Calif.). After packaging of the recombinant phage using GigaPack Gold (Stratagene), the library will be screened with the appropriate probe.

Generation of probes for cDNA library screening. A PCR-generated probe will be prepared from primers spanning the consensus NADPH binding regions of NOS by RT-PCR from OA-NOS. Briefly, RNA will be isolated from OA-NOS. First-strand CDNA synthesis will be carried out using BRL Superscript (Life Technologies, Gaithersburg, Md.), and as this enzyme has been engineered to eliminate RNAse H activity, significantly increased yields and greater full-length cDNA will be obtained. A pair of mixed oligonucleotides will be synthesized, based on the deduced nucleotide sequence of the consensus NADPH binding regions of macrophage, brain and endothelial cells as previously described by various investigators (Bredt et al., *Nature* 351:714–718, 1991; Lyons et al., *J. Biol. Chem.* 267:6370–6374, 1992; Lowenstein et al., *Proc. Natl. Acad. Sci USA* 89:6711–6715, 1992). The DNA fragment(s) amplified by PCR is expected to be approximately 350 bp. The fragment(s) will be cloned into the PCR 1000 vector (Invitrogen) for DNA sequence analysis using the dideoxynucleotide method and Taq DNA polymerase to verify the identity of the amplified product, before using this PCR product as a probe.

C) Alternatively, mixed oligonucleotides will be synthesized based on the deduced nucleotide sequence of the CNBr-generated peptides of NOS, selected according to known criteria, taking into account the degeneracy of the genetic code. A fourth alternative will be to screen the cDNA libraries with anti-NOS antiserum absorbed with *E. coli* into the pBluescript plasmid for DNA sequence analysis. The sequence data will be analyzed with the help of an IBM-PC on the Bionet computer system. Clones encoding a partial nucleotide sequence are obtained, then rescreening of the library with oligonucleotides corresponding to the furthest 5'-end of the partial clones will be performed to isolate full-length cDNA clones. Alternatively, the 5' system for rapid amplification of cDNA ends (5'-RACE-cDNA; Life Technologies) will be used to isolate full-length cDNA.

Transient expression of OA-NOS in human chondrosarcomas. The full-length CDNA of OA-NOS will be cloned in human chondrosarcomas in both the sense and antisense orientation in pcDNA-Neo expression vectors (Invitrogen, San Diego, Calif.). The cloning sites will be sequenced to confirm the orientation of the inserts. Human chondrosarcomas will be transfected using lipofectin with 10 µg of supercoiled DNA, using each of the above vectors. NOS activity in the transfected cells will be determined (at 48–72 h) by nitroblue tetrazolium reduction of NOS-transfected cells as shown by Lamas et al., (*Proc. Natl. Acad. Sci. USA* 89:6348–6352, 1992). Briefly, cells are incubated with NADPH diaphorase, and the cellular NOS enzymatic activity can be detected by its reduction of nitroblue tetrazolium to form blue-black dye formazan. Furthermore, the expressed protein will be immunoprecipitated with the available antibodies and also detected by Western blotting. Other biochemical properties of NOS activity such as inhibition by addition of NOS synthase inhibitors like L-NAME and L-NMMA and their sizes on SDS gel will be assessed. Furthermore, the reactivity of these transfected NOS will also be assessed by Western blot analysis using anti-NOS antibodies. We have obtained a full-length human chondrocyte in an expression vector and have successfully transfected it into human chondrosarcomas. The properties of this iNOS and the OA-NOS that will be cloned in the same chondrosarcoma and compared. The amino acid sequence from CNBr-generated peptide fragments from each protein will be utilized to confirm the identity of the cDNA sequence cloned from the cDNA libraries.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. An isolated inducible nitric oxide synthase (iNOS) obtainable from osteoarthritis-affected articular cartilage having the following properties:

(A) 155–160 kD in molecular weight as determined by gradient SDS-PAGE;

(B) reactive to α-ncNOS (constitutive neuronal cell nitric oxide synthase) polyclonal antibody;

(C) lack of reactivity to α-iNOS polyclonal antibody;

(D) binding calmodulin;

(E) inhibited by cycloheximide;

(F) inhibited by pyrrolidone dithiocarbamate;

(G) inhibited by 200 µM aminoguanidine and $N^G$-monomethyl-L-arginine monoacetate;

(H) inhibited by 1–3 mM aspirin;

(I) inhibited by 5–10 µM indomethacin;

(J) inhibited by 1–3 mM sodium salicylate;

(K) inducible by cytokines and endotoxin;

(L) not inhibited by transforming growth factor-β (TGFβ);

(M) not inhibited by hydrocortisone.

2. An isolated inducible nitric oxide synthase obtainable from human osteoarthritis-affected articular cartilage in accordance with claim 1.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

```
( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

ACGGAGAAGC  TTAGATCTGG  AGCAGAAGTG                                              30

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

CTGCAGGTTG  GACCACTGGA  TCCTGCCGAT                                              30

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CGGTGCTGTA  TTTCCTTACG  AGGCGAAGAA  GG                                          32

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GGTGCTGCTT  GTTAGGAGGT  CAAGTAAAGG  GC                                          32
```